US010052231B2

(12) United States Patent
Scheller et al.

(10) Patent No.: US 10,052,231 B2
(45) Date of Patent: *Aug. 21, 2018

(54) STEERABLE LASER PROBE

(71) Applicant: Katalyst Surgical, LLC, Chesterfield, MO (US)

(72) Inventors: Gregg D Scheller, Wildwood, MO (US); Matthew N Zeid, Ballwin, MO (US)

(73) Assignee: Katalyst Surgical, LLC, Chesterfield, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/596,901

(22) Filed: May 16, 2017

(65) Prior Publication Data

US 2017/0296385 A1    Oct. 19, 2017

Related U.S. Application Data

(63) Continuation of application No. 15/099,036, filed on Apr. 14, 2016, now Pat. No. 9,681,986.

(51) Int. Cl.
*A61B 18/18* (2006.01)
*A61F 9/008* (2006.01)
(Continued)

(52) U.S. Cl.
CPC .......... *A61F 9/00821* (2013.01); *A61B 18/22* (2013.01); *A61F 9/00823* (2013.01);
(Continued)

(58) Field of Classification Search
CPC ... A61F 9/00821; A61F 9/00823; A61B 18/22
(Continued)

(56) References Cited

U.S. PATENT DOCUMENTS 3,174,851 A    3/1965 Buehler et al.
4,122,853 A   10/1978 Smith
(Continued)

FOREIGN PATENT DOCUMENTS

EP    0900547 B1    3/1999
WO    WO 2011/019581 A1    2/2001
(Continued)

OTHER PUBLICATIONS

H. Fischer, B. Vogel, W. Pfleging, H. Besser, Flexible distal tip made of nitinol (NiTi) for a steerable endoscopic camera system, Materials Science and Engineering A273-275 (1999) 780-783.
(Continued)

*Primary Examiner* — William Thomson
*Assistant Examiner* — Sebastian X Lukjan
(74) *Attorney, Agent, or Firm* — Kevin P. Rollins

(57) ABSTRACT

A steerable laser probe may include a handle having a handle distal end and a handle proximal end, an auto-fixing actuation control, a flexible housing tube having a flexible housing tube distal end and a flexible housing tube proximal end, a first flexible housing tube portion having a first stiffness, and an optic fiber disposed within an inner bore of the handle and the flexible housing tube. An actuation of the auto-fixing actuation control may gradually curve the flexible housing tube. A gradual curving of the flexible housing tube may gradually curve the optic fiber.

20 Claims, 28 Drawing Sheets

(51) Int. Cl.
  *A61B 18/22* (2006.01)
  *A61B 18/20* (2006.01)
  *A61B 17/00* (2006.01)
  *A61B 18/00* (2006.01)

(52) U.S. Cl.
  CPC ..... *A61B 18/20* (2013.01); *A61B 2017/00318* (2013.01); *A61B 2017/00336* (2013.01); *A61B 2018/00589* (2013.01); *A61B 2018/2238* (2013.01); *A61F 9/008* (2013.01); *A61F 2210/009* (2013.01)

(58) Field of Classification Search
  USPC .......................................................... 606/4
  See application file for complete search history.

(56) References Cited

U.S. PATENT DOCUMENTS

| | | | |
|---|---|---|---|
| 4,147,443 A | 4/1979 | Skobel | |
| 4,687,293 A | 8/1987 | Randazzo | |
| 4,744,360 A | 5/1988 | Bath | |
| 4,870,952 A | 10/1989 | Martinez | |
| 5,190,050 A | 3/1993 | Nitzsche | |
| 5,221,279 A * | 6/1993 | Cook | A61B 18/22 606/15 |
| 5,228,852 A | 7/1993 | Goldsmith et al. | |
| 5,257,988 A | 11/1993 | L'Esperance, Jr. | |
| 5,322,055 A | 6/1994 | Davison et al. | |
| 5,322,064 A | 6/1994 | Lundquist | |
| 5,355,871 A | 10/1994 | Hurley et al. | |
| 5,381,782 A | 1/1995 | DeLaRama et al. | |
| 5,439,000 A | 8/1995 | Gunderson et al. | |
| 5,454,794 A | 10/1995 | Narciso et al. | |
| 5,520,222 A | 5/1996 | Chikama | |
| 5,735,842 A | 4/1998 | Kruege et al. | |
| 5,855,577 A | 1/1999 | Murphy-Chutorian et al. | |
| 5,873,865 A | 2/1999 | Horzewski et al. | |
| 5,951,544 A | 9/1999 | Konwitz | |
| 6,123,699 A | 9/2000 | Webster, Jr. | |
| 6,126,654 A | 10/2000 | Giba et al. | |
| 6,178,354 B1 | 1/2001 | Gibson | |
| 6,198,974 B1 | 3/2001 | Webster, Jr. | |
| 6,330,837 B1 | 12/2001 | Charles et al. | |
| 6,352,531 B1 | 3/2002 | O'Connor et al. | |
| 6,488,695 B1 | 12/2002 | Hickingbotham | |
| 6,505,530 B2 | 1/2003 | Adler et al. | |
| 6,530,913 B1 | 3/2003 | Giba et al. | |
| 6,533,772 B1 | 3/2003 | Sherts et al. | |
| 6,551,302 B1 | 4/2003 | Rosinko et al. | |
| 6,554,794 B1 | 4/2003 | Mueller et al. | |
| 6,572,608 B1 | 6/2003 | Lee et al. | |
| 6,620,153 B2 | 9/2003 | Mueller et al. | |
| 6,730,076 B2 | 5/2004 | Hickingbotham | |
| 6,863,668 B2 | 3/2005 | Gillespie et al. | |
| 6,872,214 B2 | 3/2005 | Sonnenschein et al. | |
| 6,984,230 B2 | 1/2006 | Scheller et al. | |
| 7,004,957 B1 | 2/2006 | Dampney et al. | |
| 7,226,444 B1 | 6/2007 | Ellman et al. | |
| 7,303,533 B2 | 12/2007 | Johansen et al. | |
| 7,402,158 B2 | 7/2008 | Scheller et al. | |
| 7,555,327 B2 | 6/2009 | Matlock | |
| 7,632,242 B2 | 12/2009 | Griffin et al. | |
| 7,766,904 B2 | 10/2010 | McGowan, Sr. et al. | |
| 7,935,108 B2 | 5/2011 | Baxter et al. | |
| 8,038,692 B2 | 10/2011 | Valencia et al. | |
| 8,075,553 B2 | 12/2011 | Scheller et al. | |
| 8,197,468 B2 | 6/2012 | Scheller et al. | |
| 8,840,605 B2 | 9/2014 | Scheller et al. | |
| 8,840,607 B2 | 9/2014 | Scheller et al. | |
| 8,968,277 B2 | 1/2015 | Scheller et al. | |
| 8,951,245 B2 | 2/2015 | Scheller et al. | |
| 9,023,019 B2 | 5/2015 | Scheller et al. | |
| 9,023,020 B2 | 5/2015 | Scheller et al. | |
| 9,039,686 B2 | 5/2015 | Scheller et al. | |
| 9,089,399 B2 | 7/2015 | Scheller et al. | |
| 9,107,682 B2 | 8/2015 | Scheller et al. | |
| 9,113,995 B2 | 8/2015 | Scheller et al. | |
| 9,119,702 B2 | 9/2015 | Scheller et al. | |
| 2003/0171762 A1 | 9/2003 | Forchette et al. | |
| 2004/0181138 A1 | 9/2004 | Hindricks et al. | |
| 2004/0249367 A1 | 12/2004 | Saadat et al. | |
| 2005/0054900 A1 | 3/2005 | Mawn et al. | |
| 2005/0131399 A1 | 6/2005 | Loeb et al. | |
| 2005/0154379 A1 | 7/2005 | McGowen, Sr. et al. | |
| 2005/0157985 A1 | 7/2005 | McGowan, Sr. et al. | |
| 2005/0234437 A1 | 10/2005 | Baxter et al. | |
| 2005/0272975 A1 | 12/2005 | McWeeny et al. | |
| 2005/0277874 A1 | 12/2005 | Selkee | |
| 2006/0129175 A1 | 6/2006 | Griffen et al. | |
| 2006/0178674 A1 | 8/2006 | McIntyre | |
| 2006/0293270 A1 | 12/2006 | Adamis et al. | |
| 2007/0179475 A1 | 8/2007 | Scheller | |
| 2007/0185514 A1 | 8/2007 | Kirchhevel | |
| 2007/0260231 A1 | 11/2007 | Rose et al. | |
| 2008/0132761 A1 | 6/2008 | Sonnenschein et al. | |
| 2008/0208105 A1 | 8/2008 | Zelickson et al. | |
| 2008/0287938 A1 | 11/2008 | Scheller et al. | |
| 2009/0018993 A1 | 1/2009 | Dick et al. | |
| 2009/0163943 A1 | 6/2009 | Cavanaugh et al. | |
| 2009/0187170 A1 | 7/2009 | Auld et al. | |
| 2009/0312750 A1 | 12/2009 | Spaide | |
| 2010/0004642 A1* | 1/2010 | Lumpkin | A61B 18/22 606/4 |
| 2010/0191224 A1 | 7/2010 | Butcher | |
| 2010/0268234 A1 | 10/2010 | Aho et al. | |
| 2010/0331883 A1 | 12/2010 | Schmitz et al. | |
| 2011/0028947 A1 | 2/2011 | Scheller et al. | |
| 2011/0144627 A1 | 6/2011 | Smith | |
| 2011/0144630 A1 | 6/2011 | Loeb | |
| 2011/0280653 A1 | 11/2011 | Sjostedt et al. | |
| 2012/0116361 A1 | 5/2012 | Hanlon et al. | |
| 2012/0245569 A1 | 9/2012 | Papac et al. | |
| 2013/0035551 A1 | 2/2013 | Yu et al. | |
| 2013/0060240 A1 | 3/2013 | Scheller et al. | |
| 2013/0071507 A1 | 3/2013 | Scheller et al. | |
| 2013/0090635 A1 | 4/2013 | Mansour | |
| 2013/0096541 A1 | 4/2013 | Scheller et al. | |
| 2013/0116671 A1 | 5/2013 | Scheller et al. | |
| 2013/0144278 A1 | 6/2013 | Papac et al. | |
| 2013/0150838 A1 | 6/2013 | Scheller et al. | |
| 2013/0165910 A1 | 6/2013 | Scheller et al. | |
| 2013/0261610 A1 | 10/2013 | LaConte et al. | |
| 2013/0281994 A1 | 10/2013 | Scheller et al. | |
| 2013/0304043 A1 | 11/2013 | Scheller et al. | |
| 2013/0304048 A1 | 11/2013 | Scheller et al. | |
| 2014/0005642 A1 | 1/2014 | Scheller et al. | |
| 2014/0039471 A1 | 2/2014 | Scheller et al. | |
| 2014/0039472 A1 | 2/2014 | Scheller et al. | |
| 2014/0039475 A1 | 2/2014 | Scheller et al. | |
| 2014/0046307 A1 | 2/2014 | Scheller et al. | |
| 2014/0052115 A1 | 2/2014 | Leid et al. | |
| 2014/0066907 A1 | 3/2014 | Scheller et al. | |
| 2014/0066912 A1 | 3/2014 | Scheller et al. | |
| 2014/0074073 A1 | 3/2014 | Scheller et al. | |
| 2014/0074079 A1 | 3/2014 | Scheller et al. | |
| 2014/0088572 A1 | 3/2014 | Scheller et al. | |
| 2014/0088576 A1 | 3/2014 | Scheller et al. | |
| 2014/0107628 A1 | 4/2014 | Scheller et al. | |
| 2014/0107629 A1 | 4/2014 | Scheller et al. | |
| 2015/0038950 A1 | 2/2015 | Scheller et al. | |

(56) References Cited

FOREIGN PATENT DOCUMENTS

| WO | WO 2006/091597 A1 | 8/2006 |
| WO | WO 2007/038433 A2 | 4/2007 |
| WO | WO 2013/133717    | 9/2013 |

OTHER PUBLICATIONS

Ferry P.W. Melchels, Jan Feijen, Dirk W. Grijpma, A review on stereolithography and its applications in biomedical engineering, Biomaterials 31 (2010) 6121-6130.

* cited by examiner

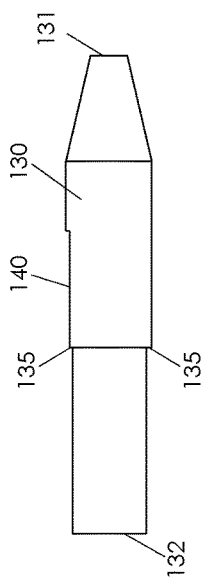
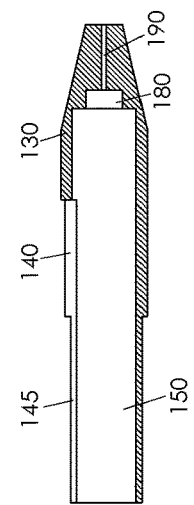
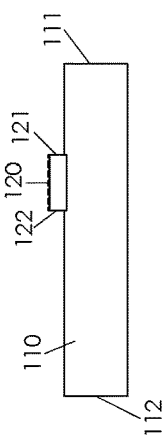
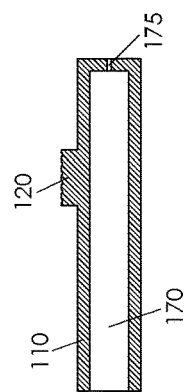
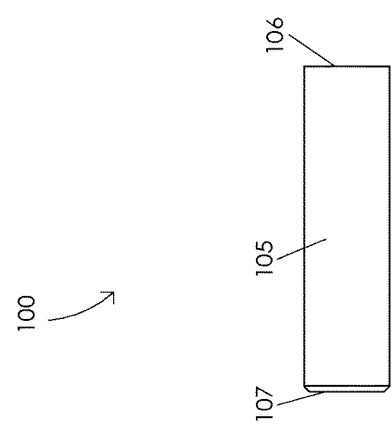
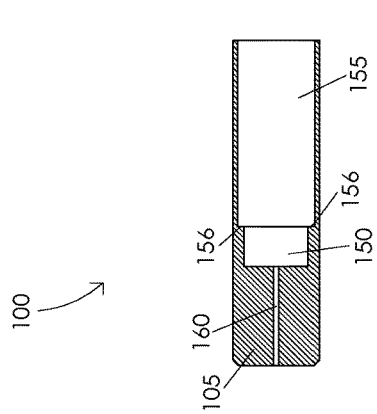
FIG. 1A
FIG. 1B

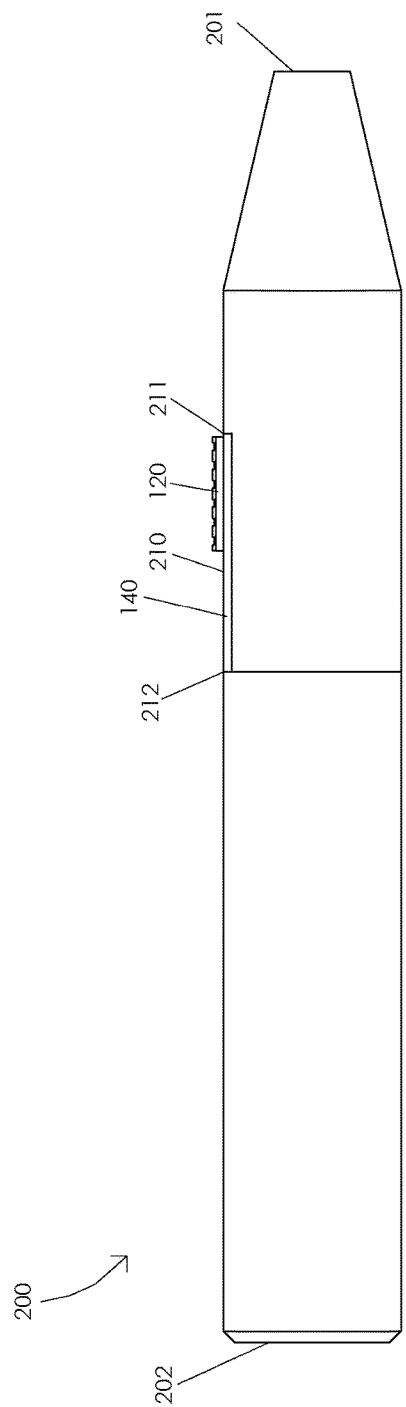
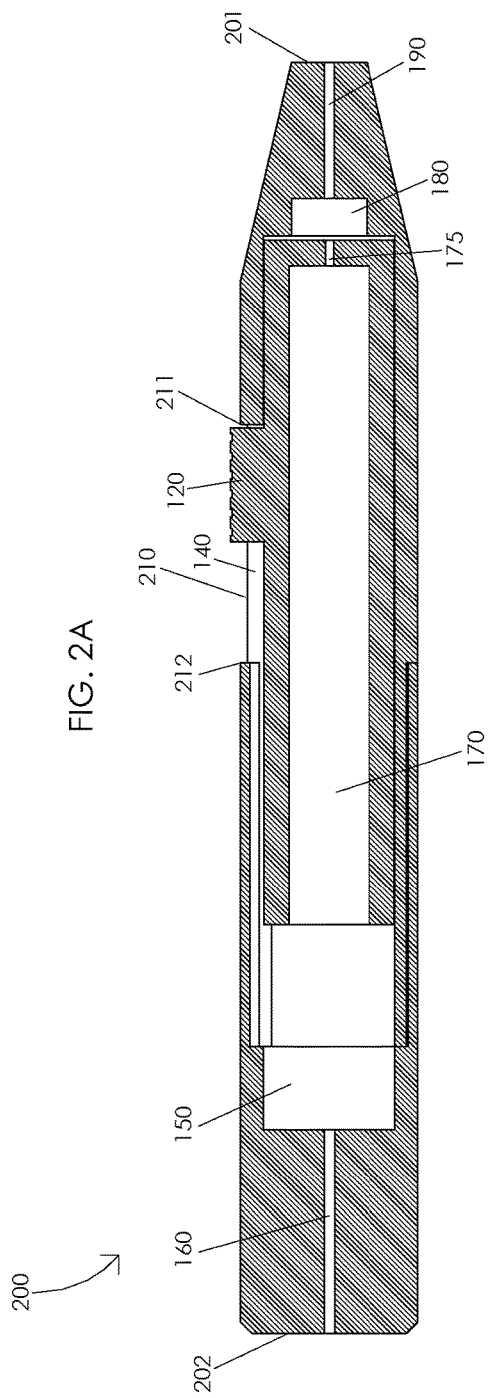
FIG. 2A
FIG. 2B

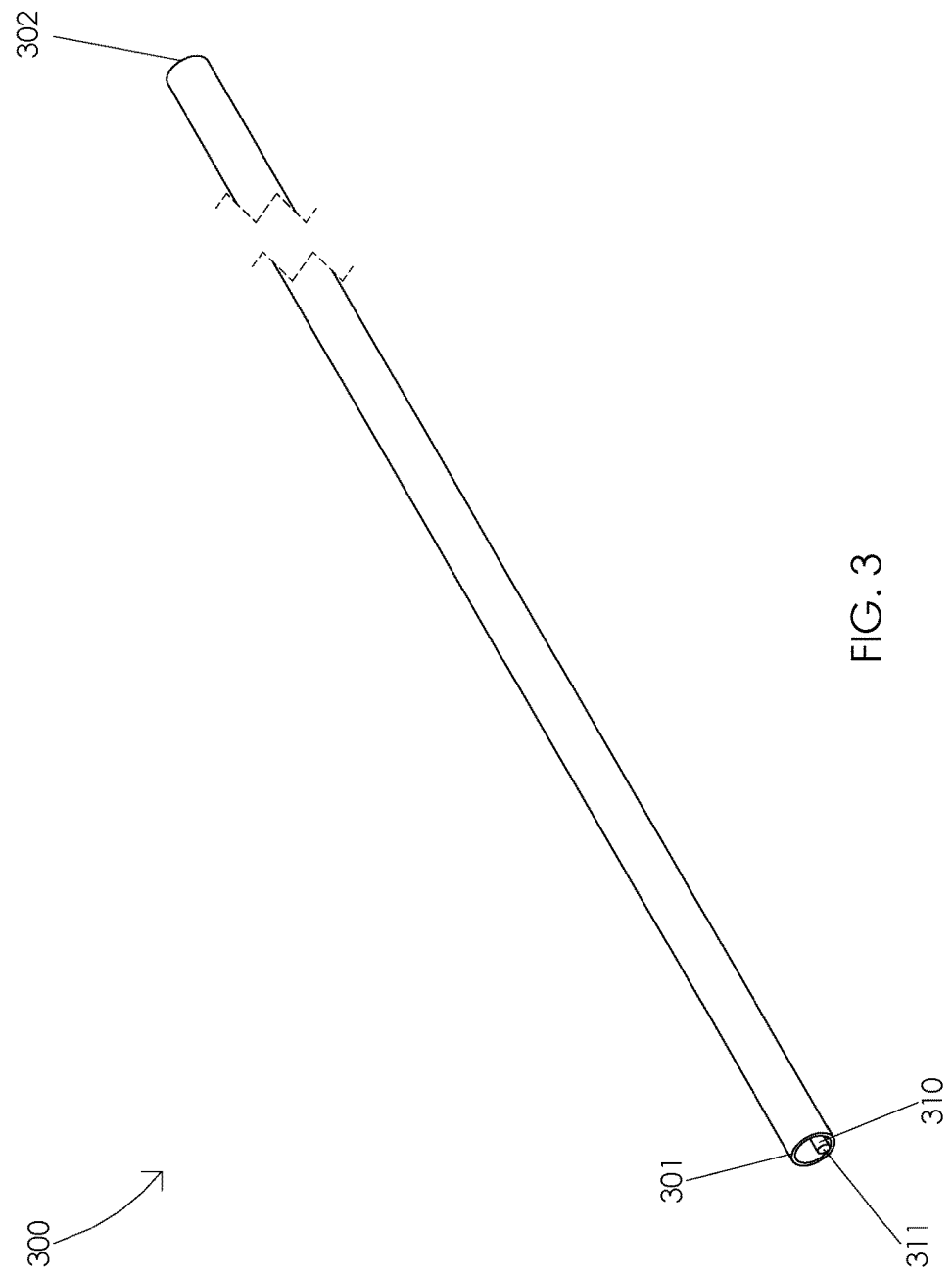

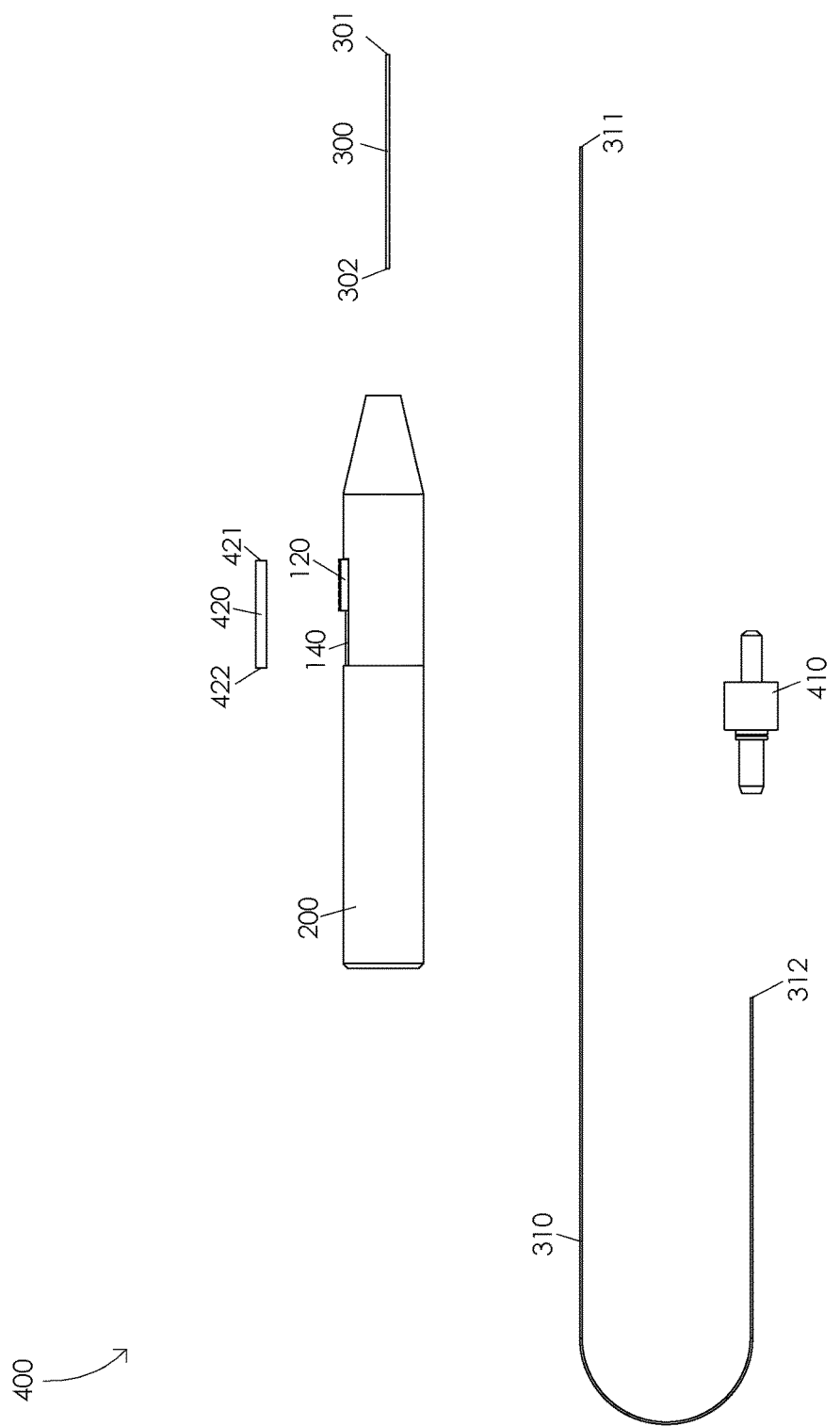

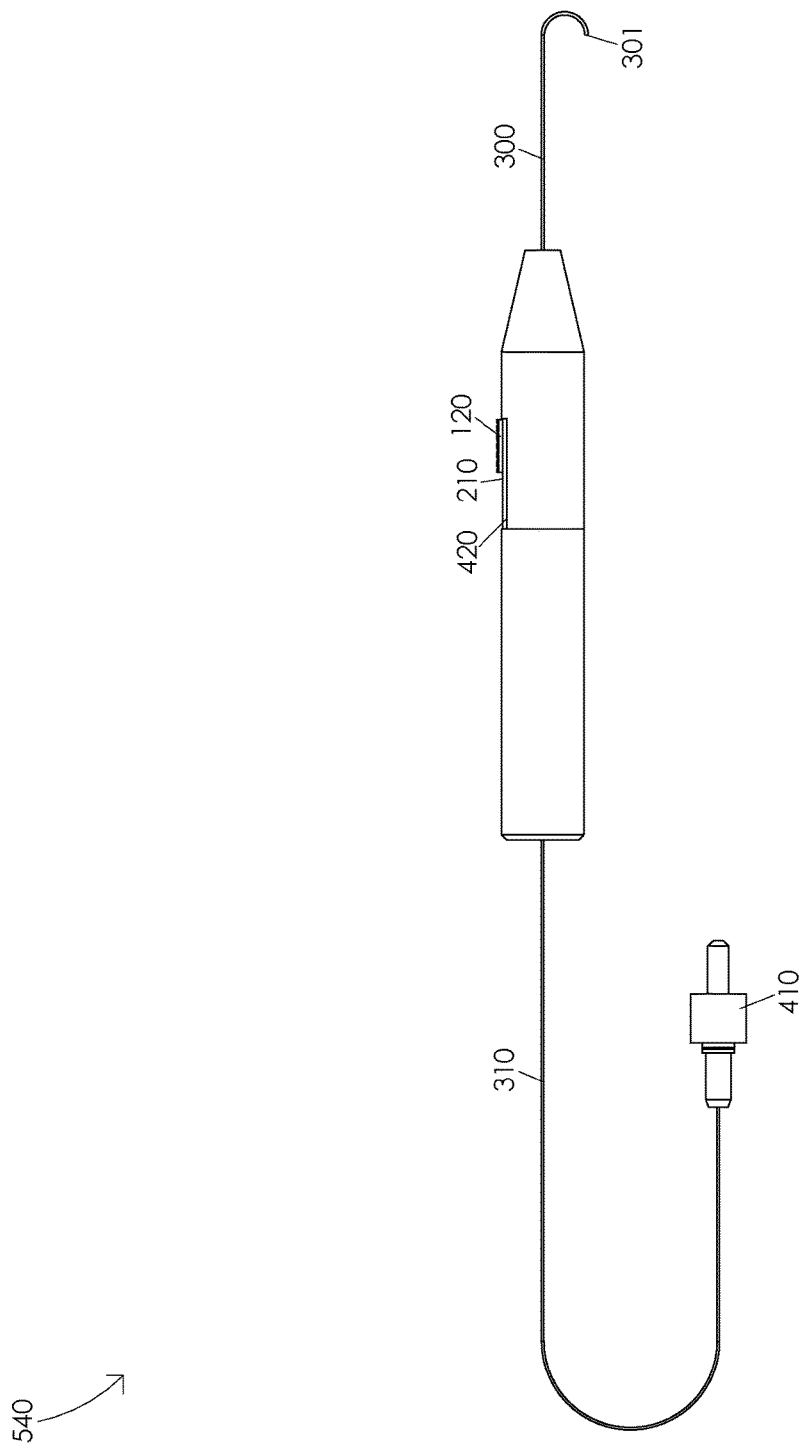

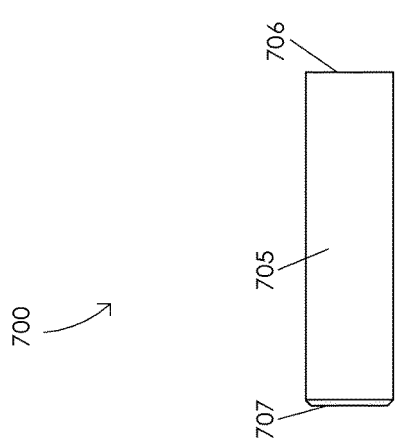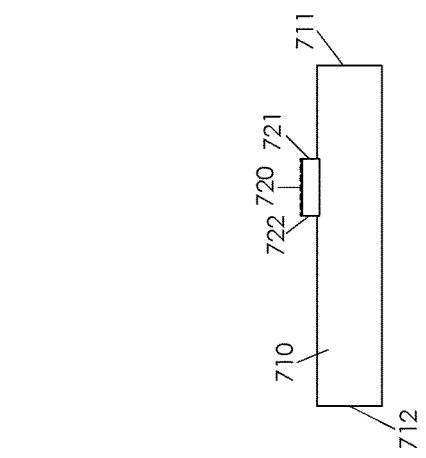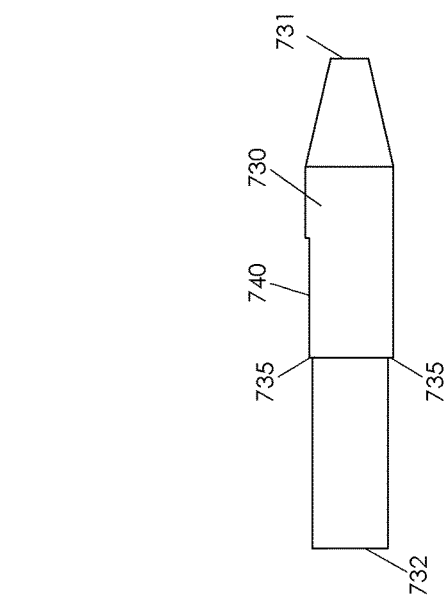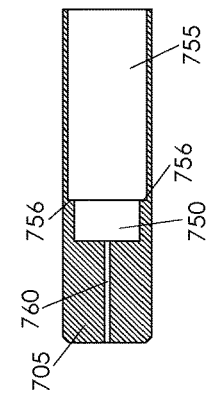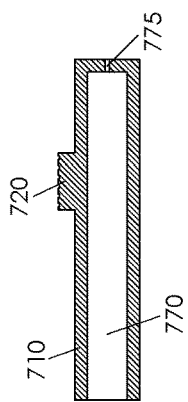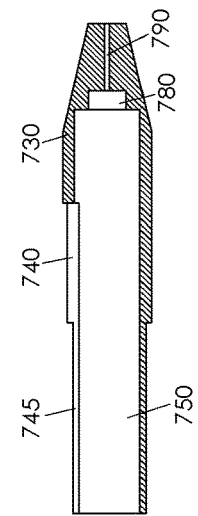
FIG. 7A
FIG. 7B

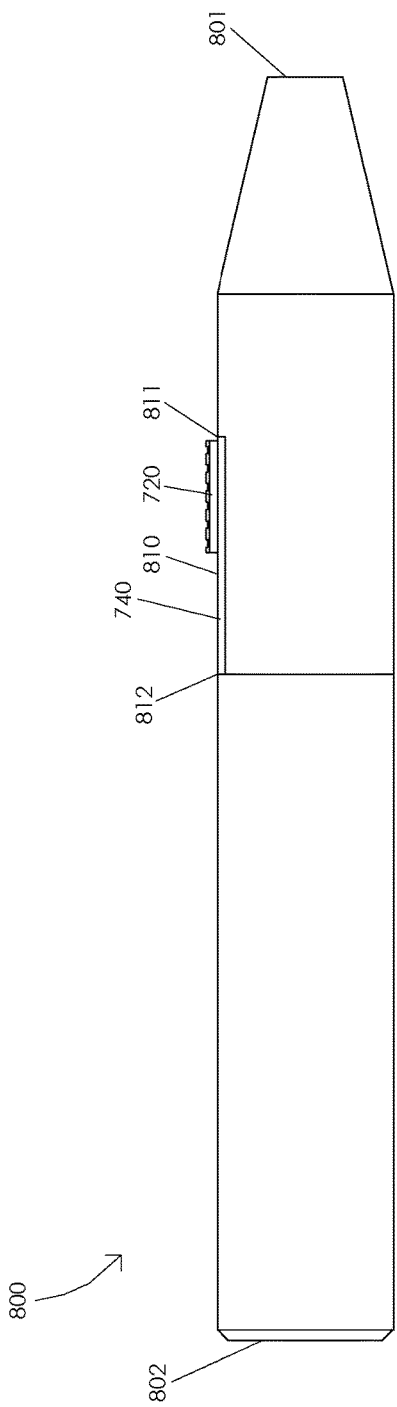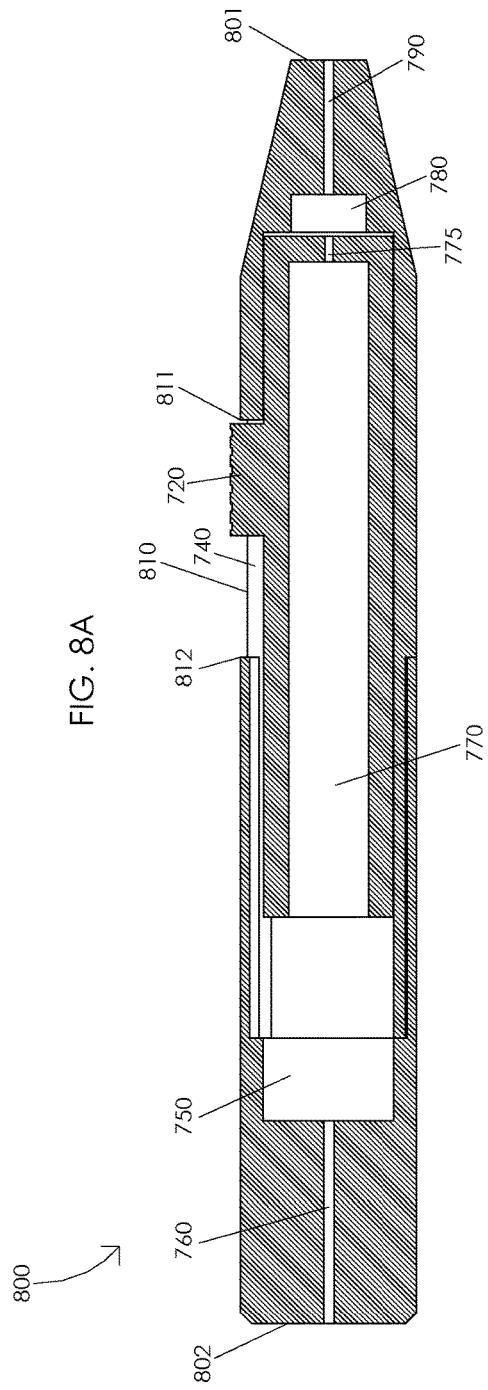
FIG. 8A
FIG. 8B

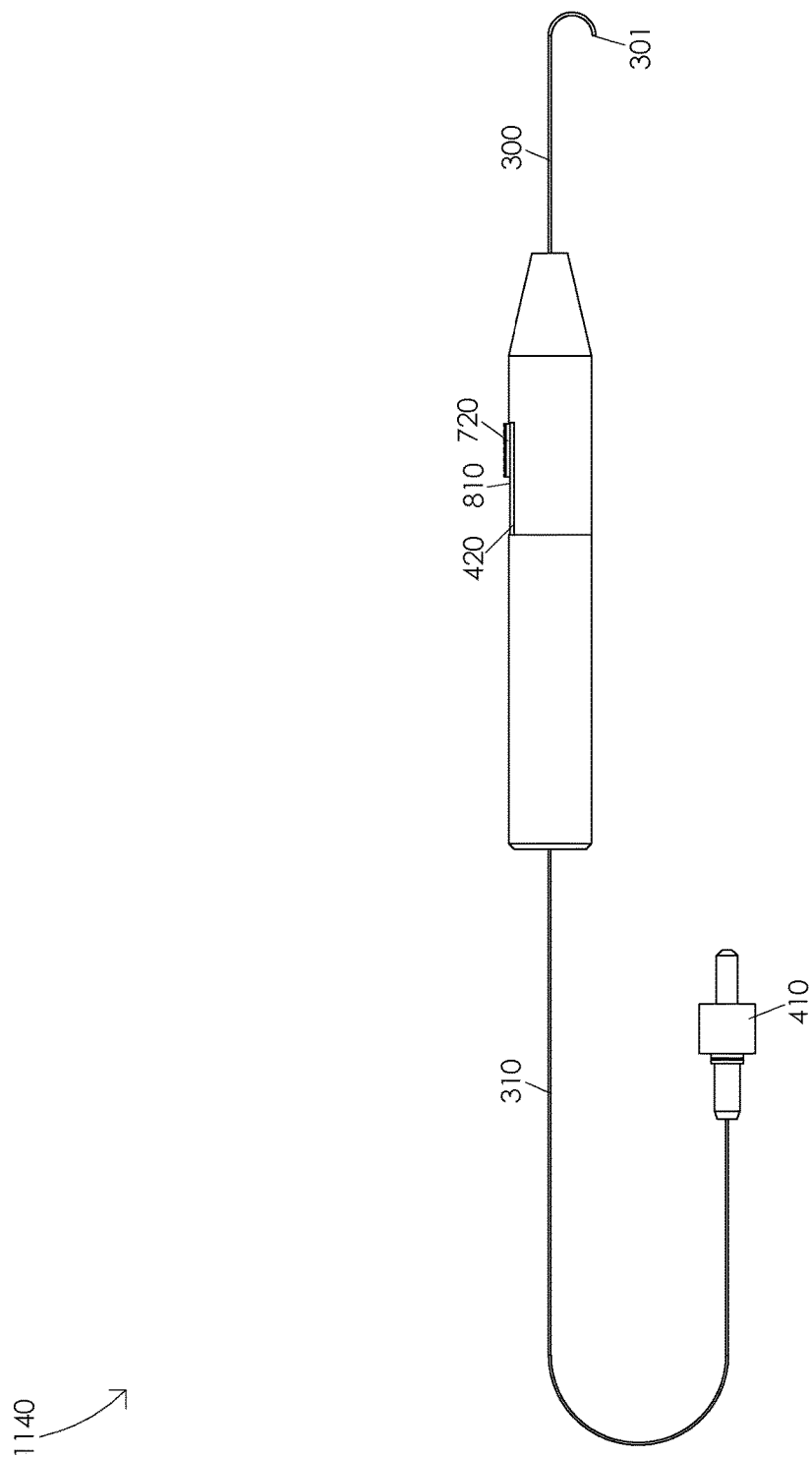

STEERABLE LASER PROBE

CROSS-REFERENCE TO RELATED APPLICATIONS

This application is a continuation of prior application Ser. No. 15/099,036, filed Apr. 14, 2016, which issued as U.S. Pat. No. 9,681,986 on Jun. 20, 2017, which is a continuation of prior application Ser. No. 13/964,158, filed Aug. 12, 2013, which issued as U.S. Pat. No. 9,351,875 on May 31, 2015, which claims the benefit of US Provisional Application No. 61/700,083, filed on Sep. 12, 2012.

FIELD OF THE INVENTION

The present disclosure relates to a surgical instrument, and, more particularly, to a steerable laser probe.

BACKGROUND OF THE INVENTION

A wide variety of ophthalmic procedures require a laser energy source. For example, ophthalmic surgeons may use laser photocoagulation to treat proliferative retinopathy. Proliferative retinopathy is a condition characterized by the development of abnormal blood vessels in the retina that grow into the vitreous humor. Ophthalmic surgeons may treat this condition by energizing a laser to cauterize portions of the retina to prevent the abnormal blood vessels from growing and hemorrhaging.

In order to increase the chances of a successful laser photocoagulation procedure, it is important that a surgeon is able aim the laser at a plurality of targets within the eye, e.g., by guiding or moving the laser from a first target to a second target within the eye. It is also important that the surgeon is able to easily control a movement of the laser. For example, the surgeon must be able to easily direct a laser beam by steering the beam to a first position aimed at a first target, guide the laser beam from the first position to a second position aimed at a second target, and hold the laser beam in the second position. Accordingly, there is a need for a surgical laser probe that can be easily guided to a plurality of targets within the eye.

BRIEF SUMMARY OF THE INVENTION

The present disclosure presents a steerable laser probe. In one or more embodiments, a steerable laser probe may comprise a handle having a handle distal end and a handle proximal end, an auto-fixing actuation control, a flexible housing tube having a flexible housing tube distal end and a flexible housing tube proximal end, and an optic fiber disposed within an inner bore of the handle and the flexible housing tube. Illustratively, an actuation of the auto-fixing actuation control may be configured to gradually curve the flexible housing tube. In one or more embodiments, a gradual curving of the flexible housing tube may be configured to gradually curve the optic fiber.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 1A and 1B are schematic diagrams illustrating an exploded view of a handle assembly;

FIGS. 2A and 2B are schematic diagrams illustrating a handle;

FIG. 3 is a schematic diagram illustrating a flexible housing tube;

FIG. 4 is a schematic diagram illustrating an exploded view of a steerable laser probe assembly;

FIGS. 5A, 5B, 5C, 5D, and 5E are schematic diagrams illustrating a gradual curving of an optic fiber;

FIGS. 7A and 7B are schematic diagrams illustrating an exploded view of a handle assembly;

FIGS. 8A and 8B are schematic diagrams illustrating a handle;

FIGS. 11A, 11B, 11C, 11D, and 11E are schematic diagrams illustrating a gradual curving of an optic fiber;

DETAILED DESCRIPTION OF AN ILLUSTRATIVE EMBODIMENT

Figure 5A:
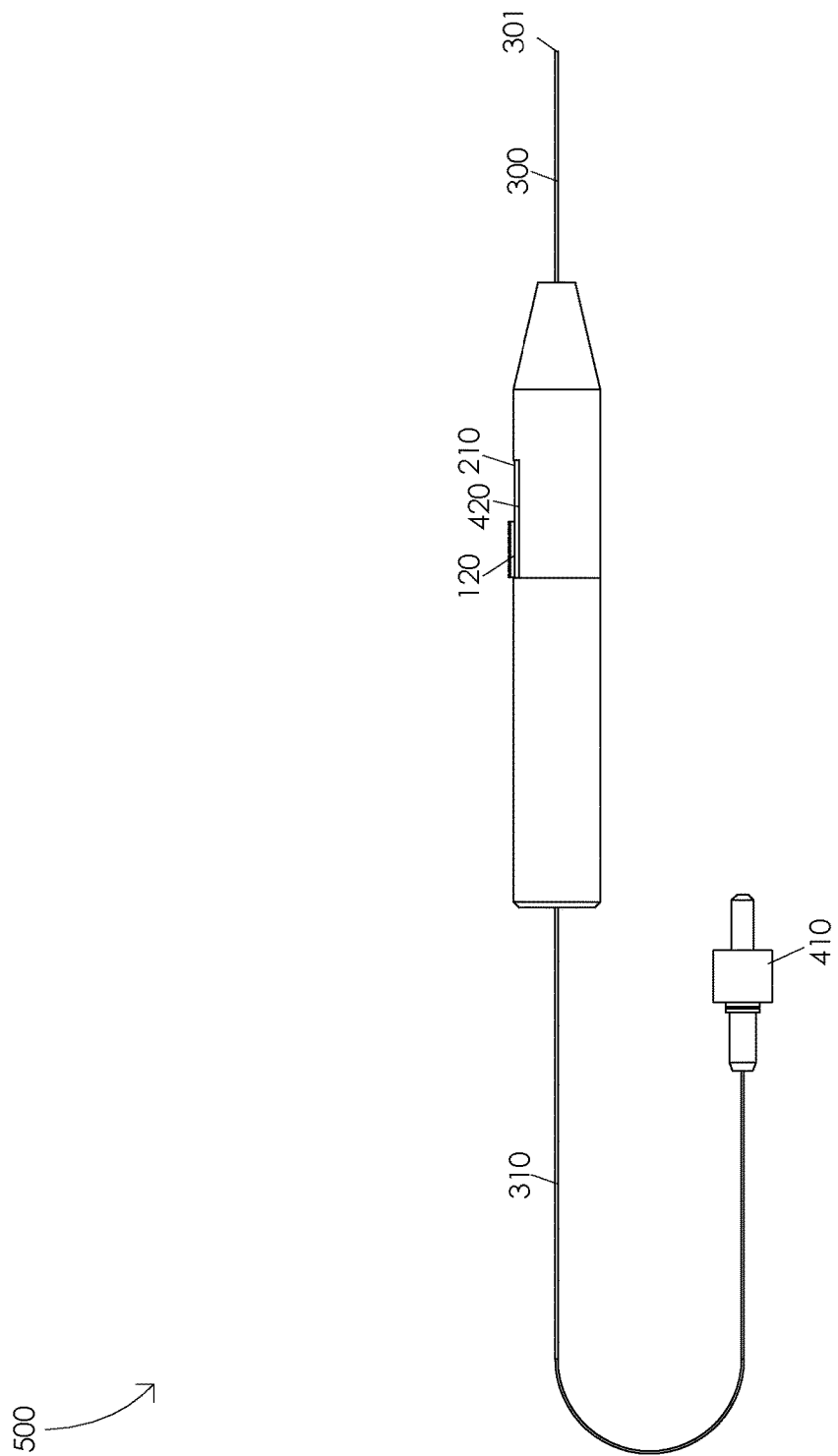

FIGS. 1A and 1B are schematic diagrams illustrating an exploded view of a handle assembly 100. FIG. 1A illustrates a side view of a handle assembly 100. Illustratively, a handle assembly 100 may comprise a handle end cap 105 having a handle end cap distal end 106 and a handle end cap proximal end 107, an actuation mechanism 110 having an actuation mechanism distal end 111 and an actuation mechanism proximal end 112, an auto-fixing actuation control 120 having an auto-fixing actuation control distal end 121 and an auto-fixing actuation control proximal end 122, a handle base 130 having a handle base distal end 131 and a handle base proximal end 132, a handle end cap interface 135, an auto-fixing component housing 140, and a handle base channel 145.

FIG. 1B illustrates a cross-sectional view of a handle assembly 100. In one or more embodiments, a handle assembly 100 may comprise an actuation mechanism guide 150, a handle base housing 155, a handle base interface 156, an optic fiber housing 160, an inner bore 170, a flexible housing tube housing 175, a distal chamber 180, and a flexible housing tube guide 190. Illustratively, handle end cap 105, actuation mechanism 110, auto-fixing actuation control 120, and handle base 130 may be manufactured from any suitable material, e.g., polymers, metals, metal alloys, etc., or from any combination of suitable materials.

FIGS. 2A and 2B are schematic diagrams illustrating a handle 200. FIG. 2A illustrates a side view of a handle 200. Illustratively, handle 200 may comprise a handle distal end 201 and a handle proximal end 202. In one or more embodiments, handle 200 may comprise an actuation control guide 210 having an actuation control guide distal end 211 and an actuation control guide proximal end 212. Illustratively, handle 200 may be manufactured from any suitable material, e.g., polymers, metals, metal alloys, etc., or from any combination of suitable materials.

FIG. 2B illustrates a cross-sectional view of a handle 200. Illustratively, actuation mechanism 110 may be disposed within handle end cap 105 and handle base 130. In one or more embodiments, a portion of handle base 130 may be disposed within handle base housing 155, e.g., handle base proximal end 132 may be disposed within handle base housing 155. Illustratively, handle base 130 may be disposed within handle base housing 155, e.g., handle base proximal end 132 may interface with handle base interface 156. For example, handle base 130 may be disposed within end cap 105 wherein end cap distal end 106 may interface with handle end cap interface 135. In one or more embodiments, handle base 130 may be fixed within handle base housing 155, e.g., by an adhesive or any suitable fixation means. For example, handle base 130 may be fixed within handle base housing 155 by a press fit, a setscrew, a weld, etc. Illustratively, handle base 130 and handle end cap 105 may be manufactured as a single unit.

In one or more embodiments, auto-fixing actuation control 120 may be disposed within actuation control guide 210. For example, auto-fixing actuation control 120 may be disposed within actuation control guide 210 wherein auto-fixing actuation control 120 adjacent to auto-fixing component housing 140. Illustratively, actuation control guide 210 may comprise a portion of handle base channel 145. In one or more embodiments, handle end cap distal end 106 may comprise actuation control guide proximal end 212. Illustratively, auto-fixing actuation control 120 may be configured to actuate within actuation control guide 210. In one or more embodiments, actuation mechanism 110 may be configured to actuate within actuation mechanism guide 150. Illustratively, an actuation of auto-fixing actuation control 120 may be configured to actuate actuation mechanism 110. In one or more embodiments, an actuation of auto-fixing actuation control 120 within actuation control guide 210 may be configured to actuate actuation mechanism 110 within actuation mechanism guide 150.

Illustratively, an actuation of auto-fixing actuation control 120 within actuation control guide 210, e.g., away from actuation control guide proximal end 212 and towards actuation control guide distal end 211, may be configured to actuate actuation mechanism 110 within actuation mechanism guide 150, e.g., away from handle proximal end 202 and towards handle distal end 201. In one or more embodiments, an extension of auto-fixing actuation control 120 relative to actuation control guide proximal end 212 may be cons figured to extend actuation mechanism 110 relative to handle proximal end 202. Illustratively, an extension of actuation mechanism 110 relative to handle proximal end 202 may be configured to extend flexible housing tube housing 175 relative to handle proximal end 202.

In one or more embodiments, an actuation of auto-fixing actuation control 120 within actuation control guide 210, e.g., away from actuation control guide distal end 211 and towards actuation control guide proximal end 212 may be configured to actuate actuation mechanism 110 within actuation guide 150, e.g., towards handle proximal end 202 and away from handle distal end 201. Illustratively, a retraction of auto-fixing actuation control 120 relative to actuation control guide proximal end 212 may be configured to retract actuation mechanism 110 relative to handle proximal end 202. In one or more embodiments, a retraction of actuation mechanism 110 relative to handle proximal end 202 may be configured to retract flexible housing tube housing 175 relative to handle proximal end 202.

FIG. 3 is a schematic diagram illustrating a flexible housing tube 300. Illustratively, flexible housing tube 300 may comprise a flexible housing tube distal end 301 and a flexible housing tube proximal end 302. Flexible housing tube 300 may be manufactured from any suitable material, e.g., polymers, metals, metal alloys, etc., or from any combination of suitable materials. Illustratively, flexible housing tube 300 may comprise a shape memory material, e.g., Nitinol. In one or more embodiments, flexible housing tube 300 may be manufactured from a material having an ultimate tensile strength between 700 and 1000 MPa. Illustratively, flexible housing tube 300 may be manufactured from a material having ultimate tensile strength less than 700 MPa or greater than 1000 MPa. In one or more embodiments, flexible housing tube 300 may be manufactured from a material having a modulus of elasticity between 30 and 80 GPa. Illustratively, flexible housing tube 300 may be manufactured from a material having a modulus of elasticity less than 30 GPa or greater than 80 GPa.

In one or more embodiments, flexible housing tube 300 may be manufactured with dimensions suitable for performing microsurgical procedures, e.g., ophthalmic surgical procedures. Illustratively, flexible housing tube 300 may be manufactured at gauge sizes commonly used in ophthalmic surgical procedures, e.g., 23 gauge, 25 gauge, etc. In one or more embodiments, flexible housing tube 300 may be configured to be inserted in a cannula, e.g., a cannula used during an ophthalmic surgical procedure. For example, one or more properties of flexible housing tube 300 may be optimized to reduce friction as flexible housing tube 300 is inserted into a cannula. In one or more embodiments, one or more properties of flexible housing tube 300 may be optimized to reduce friction as flexible housing tube 300 is removed from a cannula. Illustratively, flexible housing tube 300 may have an ultimate tensile strength between 1000 MPa and 1100 MPa. In one or more embodiments, flexible housing tube 300 may have an ultimate tensile strength less than 1000 MPa or greater than 1100 MPa.

In one or more embodiments, an optic fiber 310 may be disposed within flexible housing tube 300. Illustratively, optic fiber 310 may comprise an optic fiber distal end 311 and an optic fiber proximal end 312. In one or more embodiments, optic fiber 310 may be configured to transmit light, e.g., laser light. Illustratively, optic fiber 310 may be disposed within flexible housing tube 300 wherein optic fiber distal end 311 may be adjacent to flexible housing tube distal end 301. In one or more embodiments, a portion of optic fiber 310 may be fixed to a portion of flexible housing tube 300, e.g., by an adhesive or any suitable fixation means.

FIG. 4 is a schematic diagram illustrating an exploded view of a steerable laser probe assembly 400. In one or more embodiments, a steerable laser probe assembly 400 may comprise a handle 200, a flexible housing tube 300 having a flexible housing tube distal end 301 and a flexible housing tube proximal end 302, an optic fiber 310 having an optic fiber distal end 311 and an optic fiber proximal end 312, an auto-fixing component 420 having an auto-fixing component distal end 421 and an auto-fixing component proximal end 422, and a light source interface 410. Illustratively, light source interface 410 may be configured to interface with optic fiber 310, e.g., at optic fiber proximal end 312. In one or more embodiments, light source interface 410 may comprise a standard light source connector, e.g., an SMA connector.

Illustratively, flexible housing tube 300 may be disposed within flexible housing tube housing 175, actuation mechanism guide 150, and flexible housing tube guide 190. In one or more embodiments, a portion of flexible housing tube 300 may be fixed within flexible housing tube housing 175, e.g., flexible housing tube proximal end 302 may be fixed within flexible housing tube housing 175. Illustratively, a portion of flexible housing tube 300 may be fixed within flexible housing tube housing 175, e.g., by an adhesive or any suitable fixation means. For example, a portion of flexible housing tube 300 may be fixed within flexible housing tube housing 175 by a press fit, a set screw, etc. In one or more embodiments, flexible housing tube 300 may be fixed within flexible housing tube housing 175 wherein flexible housing tube distal end 301 extends from handle distal end 201.

Illustratively, optic fiber 310 may be disposed within optic fiber housing 160, actuation mechanism guide 150, inner bore 170, flexible housing tube 300, and flexible housing tube guide 190. In one or more embodiments, optic fiber 310 may be disposed within flexible housing tube 300 wherein optic fiber distal end 311 may be adjacent to flexible housing tube distal end 301. Illustratively, a portion of optic fiber 310 may be fixed within flexible housing tube 300, e.g., by an adhesive or any suitable fixation means. In one or more embodiments, a portion of optic fiber 310 may be fixed within optic fiber housing 160, e.g., by an adhesive or any suitable fixation means. Illustratively, optic fiber 310 may be fixed within optic fiber housing 160 and optic fiber 310 may be fixed to a portion of flexible housing tube 300.

In one or more embodiments, an actuation of auto-fixing actuation control 120 within actuation control guide 210, e.g., towards actuation control guide distal end 211 and away from actuation control guide proximal end 212, may be configured to actuate actuation mechanism 110 within actuation mechanism guide 150, e.g., towards handle distal end 201 and away from handle proximal end 202. Illustratively, an extension of auto-fixing actuation control 120 relative to actuation control guide proximal end 212 may be configured to extend actuation mechanism 110 relative to handle proximal end 202. In one or more embodiments, an extension of actuation mechanism 110 relative to handle proximal end 202 may be configured to extend flexible housing tube housing 175 relative to handle proximal end 202. Illustratively, an extension of flexible housing tube housing 175 relative to handle proximal end 202 may be configured to extend flexible housing tube 300 relative to handle proximal end 202. In one or more embodiments, an extension of flexible housing tube 300 relative to handle proximal end 202 may be configured to extend flexible housing tube 300 relative to optic fiber 310. Illustratively, a portion of optic fiber 310, e.g., a portion of optic fiber 310 fixed to flexible housing tube 300, may be configured to resist an extension of flexible housing tube 300 relative to optic fiber 310. In one or more embodiments, optic fiber 310 may be configured to prevent flexible housing tube 300 from extending relative to optic fiber 310. Illustratively, an extension of flexible housing tube 300 relative to optic fiber 310 may be configured to apply a force to a portion of flexible housing tube 300. In one or more embodiments, an application of a force to a portion of flexible housing tube 300 may be configured to compress a portion of flexible housing tube 300. Illustratively, a compression of a portion of flexible housing tube 300 may be configured to cause flexible housing tube 300 to gradually curve. In one or more embodiments, a gradual curving of flexible housing tube 300 may be configured to gradually curve optic fiber 310.

In one or more embodiments, an actuation of auto-fixing actuation control 120 within actuation control guide 210, e.g., towards actuation control guide proximal end 212 and away from actuation control guide distal end 211, may be configured to actuate actuation mechanism 110 within actuation mechanism guide 150, e.g., towards handle proximal end 202 and away from handle distal end 201. Illustratively, a retraction of auto-fixing actuation control 120 relative to actuation control guide proximal end 212 may be configured to retract actuation mechanism 110 relative to handle proximal end 202. In one or more embodiments, a retraction of actuation mechanism 110 relative to handle proximal end 202 may be configured to retract flexible housing tube housing 175 relative to handle proximal end 202. Illustratively, a retraction of flexible housing tube housing 175 relative to handle proximal end 202 may be configured to retract flexible housing tube 300 relative to handle proximal end 202. In one or more embodiments, a retraction of flexible housing tube 300 relative to handle proximal end 202 may be configured to retract flexible housing tube 300 relative to optic fiber 310. Illustratively, a portion of optic fiber 310, e.g., a portion of optic fiber 310 fixed to flexible housing tube 300, may be configured to facilitate a retraction of flexible housing tube 300 relative to optic fiber 310. In one or more embodiments, a retraction of flexible housing tube 300 relative to optic fiber 310 may be configured to reduce a force applied to a portion of flexible housing tube 300. Illustratively, a reduction of a force applied to a portion of flexible housing tube 300 may be configured to decompress a portion of flexible housing tube 300. In one or more embodiments, a decompression of a portion of flexible housing tube 300 may be configured to cause flexible housing tube 300 to gradually straighten. Illustratively, a gradual straightening of flexible housing tube 300 may be configured to gradually straighten optic fiber 310.

In one or more embodiments, auto-fixing component 420 may be disposed within auto-fixing component housing 140. Illustratively, auto-fixing component 420 may be fixed within auto-fixing component housing 140, e.g., by an adhesive or any suitable fixation means. In one or more embodiments, auto-fixing component 420 may be disposed within auto-fixing component housing 140 wherein a portion of auto-fixing component 420 may be adjacent to a portion of auto-fixing actuation control 120. Illustratively, auto-fixing component 420 may be configured to produce a magnetic field, e.g., auto-fixing component 420 may comprise a permanent magnet. In one or more embodiments, auto-fixing component 420 may comprise a ferromagnetic material, e.g., auto-fixing component 420 may comprise a ferrimagnetic material. Illustratively, auto-fixing actuation control 120 may be configured to produce a magnetic field, e.g., auto-fixing actuation control 120 may comprise a permanent magnetic. In one or more embodiments, auto-fixing actuation control 120 may comprise a ferromagnetic material, e.g., auto-fixing actuation control 120 may comprise a ferrimagnetic material. Illustratively, auto-fixing component 420 may be configured to temporarily fix auto-fixing actuation control 120 in a position within actuation control guide 210, e.g., a magnetic force attracting auto-fixing actuation control 120 to auto-fixing component 420 may be configured to hold auto-fixing actuation control 120 fixed in a position within actuation control guide 210. In one or more embodiments, auto-fixing actuation control 120 may be configured to temporarily fix auto-fixing actuation control 120 in a position within actuation control guide 210, e.g., a magnetic force attracting auto-fixing component 420 to auto-fixing actuation control 120 may be configured to temporarily hold auto-fixing actuation control 120 fixed in a position within actuation control guide 210. Illustratively, both auto-fixing component 420 and auto-fixing actuation control 120 may be configured to temporarily fix auto-fixing actuation control 120 in a position within actuation control guide 210, e.g., auto-fixing component 420 and auto-fixing actuation control 120 may both comprise permanent magnets having poles oriented to attract auto-fixing component 420 to auto-fixing actuation control 120 and to attract auto-fixing actuation control 120 to auto-fixing component 420.

In one or more embodiments, a surgeon may actuate auto-fixing actuation control 120 within actuation control guide 210, e.g., by applying a force to a portion of auto-fixing actuation control 120 until auto-fixing actuation control 120 is in a first desired position within actuation control guide 210. Illustratively, the surgeon may then remove the force applied to auto-fixing actuation control 120 and perform a portion of a surgical procedure, e.g., auto-fixing actuation control 120 and auto-fixing component 420 may be configured to temporarily fix auto-fixing actuation control 120 in the first desired position within actuation control guide 210. In one or more embodiments, the surgeon may actuate auto-fixing actuation control 120 within actuation control guide 210, e.g., by applying a force to a portion of auto-fixing actuation control 120 until auto-fixing actuation control 120 is in a second desired position within actuation control guide 210. Illustratively, the surgeon may then remove the force applied to auto-fixing actuation control 120 and perform a portion of a surgical procedure, e.g., auto-fixing actuation control 120 and auto-fixing component 420 may be configured to temporarily fix auto-fixing actuation control 120 in the second desired position within actuation control guide 210. In one or more embodiments, the surgeon may actuate auto-fixing actuation control 120 within actuation control guide 210, e.g., by applying a force to a portion of auto-fixing actuation control 120 until auto-fixing actuation control 120 is in a third desired position within actuation control guide 210. Illustratively, the surgeon may then remove the force applied to auto-fixing actuation control 120 and perform a portion of a surgical procedure, e.g., auto-fixing actuation control 120 and auto-fixing component 420 may be configured to temporarily fix auto-fixing actuation control 120 in the third desired position within actuation control guide 210. In one or more embodiments, auto-fixing actuation control 120 and auto-fixing component 420 may be configured to temporarily fix auto-fixing actuation control 120 in any desired position within actuation control guide 210.

FIGS. 5A, 5B, 5C, 5D, and 5E are schematic diagrams illustrating a gradual curving of an optic fiber 310. FIG. 5A illustrates a straight optic fiber 500. In one or more embodiments, optic fiber 310 may comprise a straight optic fiber 500, e.g., when flexible housing tube 300 is fully retracted relative to optic fiber 310. Illustratively, optic fiber 310 may comprise a straight optic fiber 500, e.g., when auto-fixing actuation control 120 is fully retracted relative to actuation control guide proximal end 212. In one or more embodiments, optic fiber 310 may comprise a straight optic fiber 500, e.g., when actuation mechanism 110 is fully retracted relative to handle proximal end 202. Illustratively, a line tangent to optic fiber distal end 311 may be parallel to a line tangent to flexible housing tube proximal end 302, e.g., when optic fiber 310 comprises a straight optic fiber 500. In one or more embodiments, auto-fixing actuation control 120 and auto-fixing component 420 may be configured to temporarily fix auto-fixing actuation control 120 in a first fixed position within actuation control guide 210. Illustratively, optic fiber 310 may comprise a straight optic fiber 500, e.g., when auto-fixing actuation control 120 is fixed in the first fixed position within actuation control guide 210.

Figure 5B:
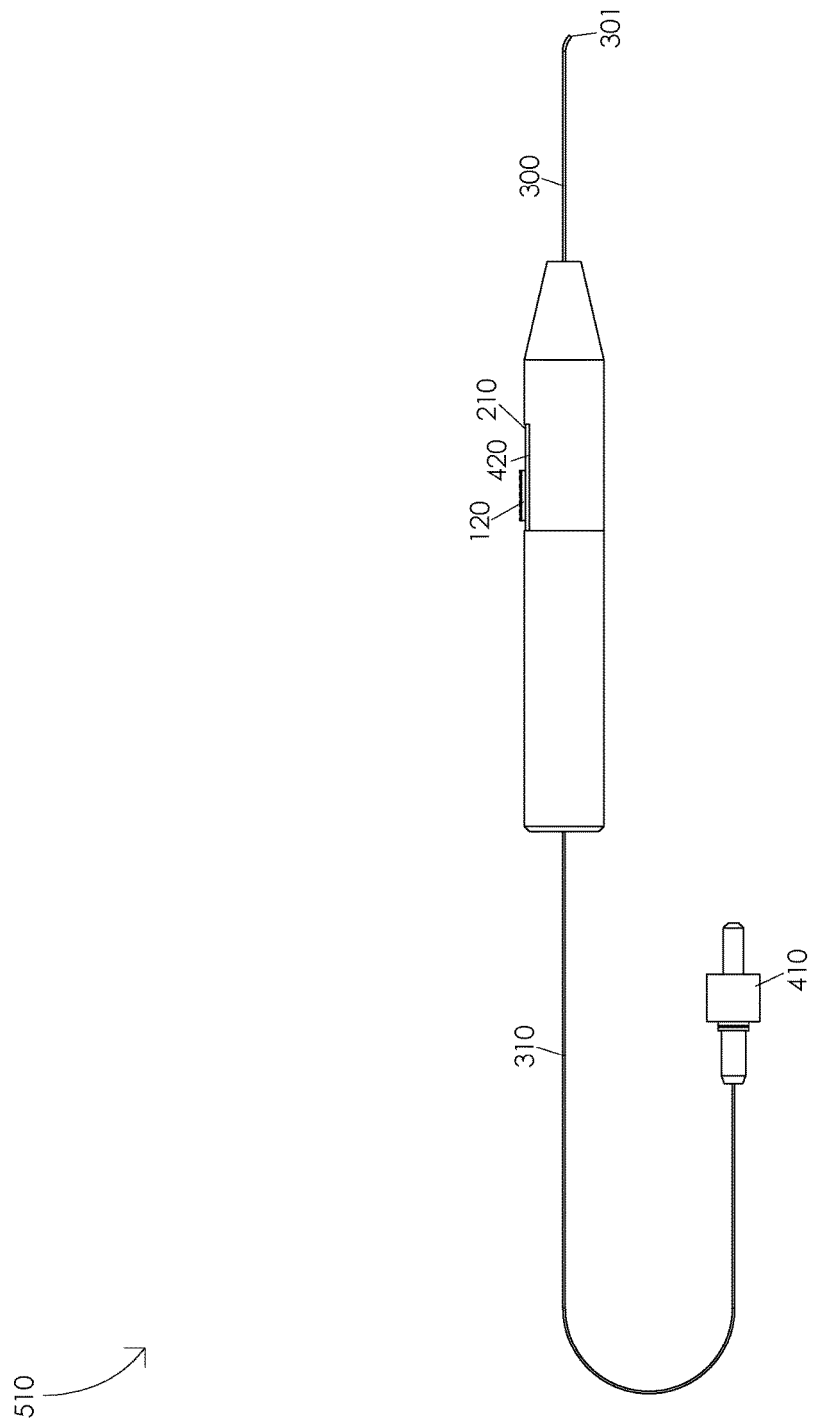

FIG. 5B illustrates an optic fiber in a first curved position 510. In one or more embodiments, an extension of auto-fixing actuation control 120 relative to actuation control guide proximal end 212 may be configured to gradually curve optic fiber 310 from a straight optic fiber 500 to an optic fiber in a first curved position 510. Illustratively, an extension of auto-fixing actuation control 120 relative to actuation control guide proximal end 212 may be configured to extend actuation mechanism 110 relative to handle proximal end 202. In one or more embodiments, an extension of actuation mechanism 110 relative to handle proximal end 202 may be configured to extend flexible housing tube 300 relative to optic fiber 310. Illustratively, a portion of optic fiber 310, e.g., a portion of optic fiber 310 fixed to flexible housing tube 300, may be configured to resist an extension of flexible housing tube 300 relative to optic fiber 310. In one or more embodiments, a portion of optic fiber 310 may be configured to apply a force to a portion of flexible housing tube 300, e.g., to resist an extension of flexible housing tube 300 relative to optic fiber 310. Illustratively, an application of a force to a portion of flexible housing tube 300 may be configured to compress a portion of flexible housing tube 300. In one or more embodiments, a compression of a portion of flexible housing tube 300 may cause flexible housing tube 300 to gradually curve. Illustratively, a gradual curving of flexible housing tube 300 may be configured to gradually curve optic fiber 310, e.g., from a straight optic fiber 500 to an optic fiber in a first curved position 510. In one or more embodiments, a line tangent to optic fiber distal end 311 may intersect a line tangent to flexible housing tube proximal end 302 at a first angle, e.g., when optic fiber 310 comprises an optic fiber in a first curved position 510. In one or more embodiments, the first angle may comprise any angle greater than zero degrees. For example, the first angle may comprise a 45 degree angle. Illustratively, auto-fixing actuation control 120 and auto-fixing component 420 may be configured to temporarily fix auto-fixing actuation control 120 in a second fixed position within actuation control guide 210. In one or more embodiments, optic fiber 310 may comprise an optic fiber in a first curved position 510, e.g., when auto-fixing actuation control 120 is fixed in the second fixed position within actuation control guide 210.

Figure 5C:
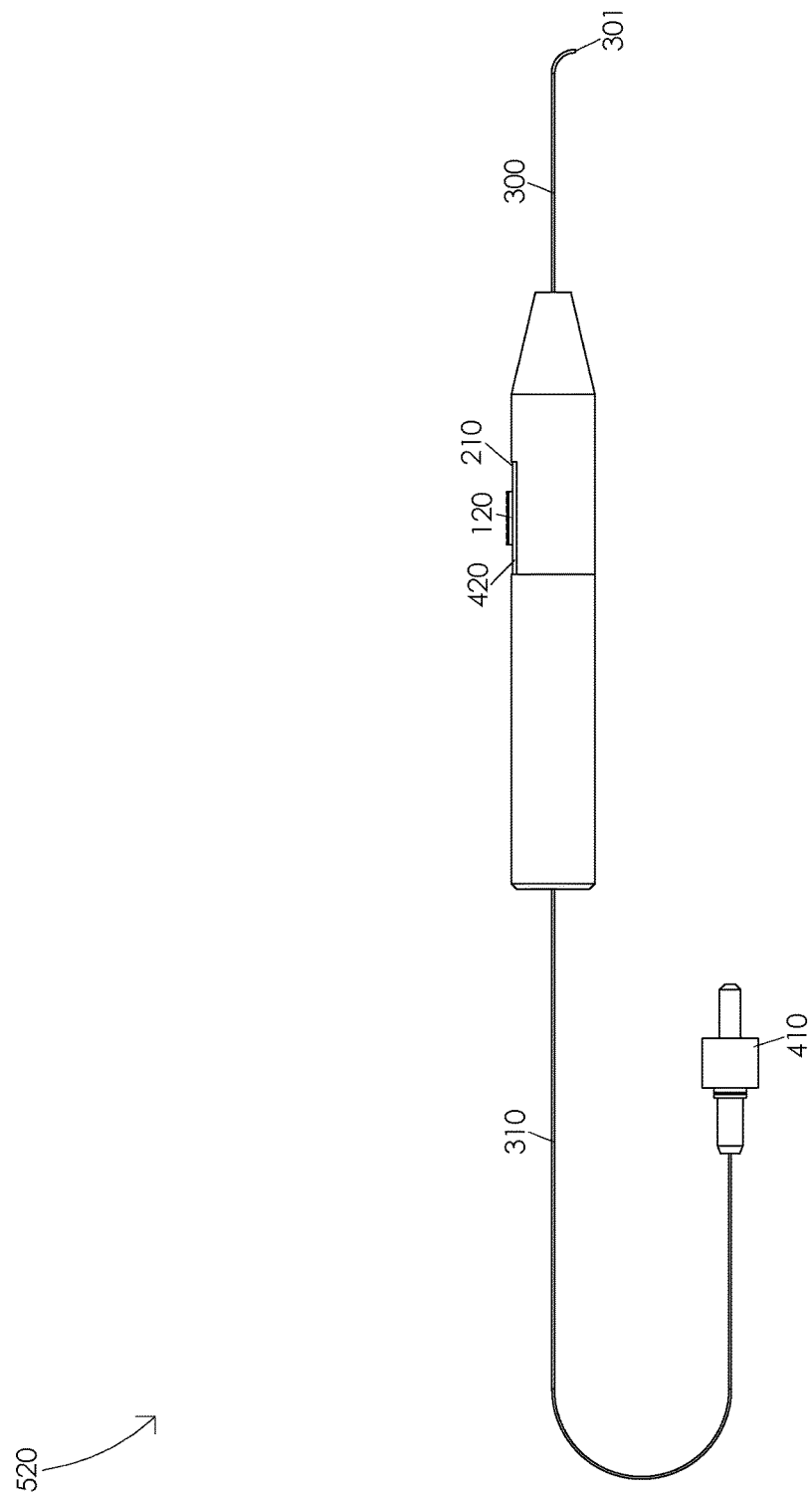

FIG. 5C illustrates an optic fiber in a second curved position 520. In one or more embodiments, an extension of auto-fixing actuation control 120 relative to actuation control guide proximal end 212 may be configured to gradually curve optic fiber 310 from an optic fiber in a first curved position 510 to an optic fiber in a second curved position 520. Illustratively, an extension of auto-fixing actuation control 120 relative to actuation control guide proximal end 212 may be configured to extend actuation mechanism 110 relative to handle proximal end 202. In one or more embodiments, an extension of actuation mechanism 110 relative to handle proximal end 202 may be configured to extend flexible housing tube 300 relative to optic fiber 310. Illustratively, a portion of optic fiber 310, e.g., a portion of optic fiber 310 fixed to flexible housing tube 300, may be configured to resist an extension of flexible housing tube 300 relative to optic fiber 310. In one or more embodiments, a portion of optic fiber 310 may be configured to apply a force to a portion of flexible housing tube 300, e.g., to resist an extension of flexible housing tube 300 relative to optic fiber 310. Illustratively, an application of a force to a portion of flexible housing tube 300 may be configured to compress a portion of flexible housing tube 300. In one or more embodiments, a compression of a portion of flexible housing tube 300 may cause flexible housing tube 300 to gradually curve. Illustratively, a gradual curving of flexible housing tube 300 may be configured to gradually curve optic fiber 310, e.g., from an optic fiber in a first curved position 510 to an optic fiber in a second curved position 520. In one or more embodiments, a line tangent to optic fiber distal end 311 may intersect a line tangent to flexible housing tube proximal end 302 at a second angle, e.g., when optic fiber 310 comprises an optic fiber in a second curved position 520. In one or more embodiments, the second angle may comprise any angle greater than the first angle. For example, the second angle may comprise a 90 degree angle. Illustratively, auto-fixing actuation control 120 and auto-fixing component 420 may be configured to temporarily fix auto-fixing actuation control 120 in a third fixed position within actuation control guide 210. In one or more embodiments, optic fiber 310 may comprise an optic fiber in a second curved position 520, e.g., when auto-fixing actuation control 120 is fixed in the third fixed position within actuation control guide 210.

Figure 5D:
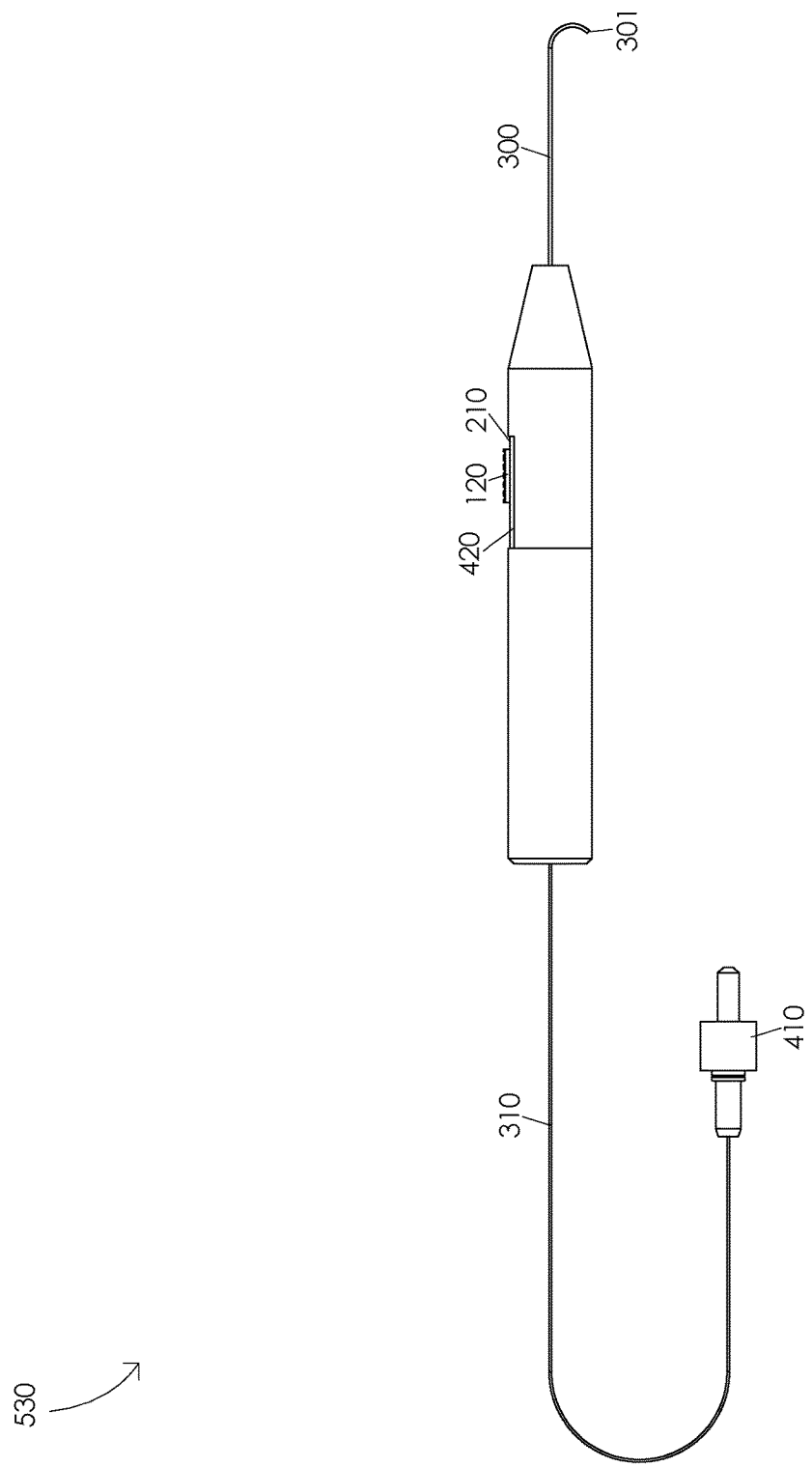

FIG. 5D illustrates an optic fiber in a third curved position 530. In one or more embodiments, an extension of auto-fixing actuation control 120 relative to actuation control guide proximal end 212 may be configured to gradually curve optic fiber 310 from an optic fiber in a second curved position 520 to an optic fiber in a third curved position 530. Illustratively, an extension of auto-fixing actuation control 120 relative to actuation control guide proximal end 212 may be configured to extend actuation mechanism 110 relative to handle proximal end 202. In one or more embodiments, an extension of actuation mechanism 110 relative to handle proximal end 202 may be configured to extend flexible housing tube 300 relative to optic fiber 310. Illustratively, a portion of optic fiber 310, e.g., a portion of optic fiber 310 fixed to flexible housing tube 300, may be configured to resist an extension of flexible housing tube 300 relative to optic fiber 310. In one or more embodiments, a portion of optic fiber 310 may be configured to apply a force to a portion of flexible housing tube 300, e.g., to resist an extension of flexible housing tube 300 relative to optic fiber 310. Illustratively, an application of a force to a portion of flexible housing tube 300 may be configured to compress a portion of flexible housing tube 300. In one or more embodiments, a compression of a portion of flexible housing tube 300 may cause flexible housing tube 300 to gradually curve. Illustratively, a gradual curving of flexible housing tube 300 may be configured to gradually curve optic fiber 310, e.g., from an optic fiber in a second curved position 520 to an optic fiber in a third curved position 530. In one or more embodiments, a line tangent to optic fiber distal end 311 may intersect a line tangent to flexible housing tube proximal end 302 at a third angle, e.g., when optic fiber 310 comprises an optic fiber in a third curved position 530. In one or more embodiments, the third angle may comprise any angle greater than the second angle. For example, the third angle may comprise a 135 degree angle. Illustratively, autos fixing actuation control 120 and auto-fixing component 420 may be configured to temporarily fix auto-fixing actuation control 120 in a fourth fixed position within actuation control guide 210. In one or more embodiments, optic fiber 310 may comprise an optic fiber in a third curved position 530, e.g., when auto-fixing actuation control 120 is fixed in the fourth fixed position within actuation control guide 210.

FIG. 5E illustrates an optic fiber in a fourth curved position 540. In one or more embodiments, an extension of auto-fixing actuation control 120 relative to actuation control guide proximal end 212 may be configured to gradually curve optic fiber 310 from an optic fiber in a third curved position 530 to an optic fiber in a fourth curved position 540. Illustratively, an extension of auto-fixing actuation control 120 relative to actuation control guide proximal end 212 may be configured to extend actuation mechanism 110 relative to handle proximal end 202. In one or more embodiments, an extension of actuation mechanism 110 relative to handle proximal end 202 may be configured to extend flexible housing tube 300 relative to optic fiber 310. Illustratively, a portion of optic fiber 310, e.g., a portion of optic fiber 310 fixed to flexible housing tube 300, may be configured to resist an extension of flexible housing tube 300 relative to optic fiber 310. In one or more embodiments, a portion of optic fiber 310 may be configured to apply a force to a portion of flexible housing tube 300, e.g., to resist an extension of flexible housing tube 300 relative to optic fiber 310. Illustratively, an application of a force to a portion of flexible housing tube 300 may be configured to compress a portion of flexible housing tube 300. In one or more embodiments, a compression of a portion of flexible housing tube 300 may cause flexible housing tube 300 to gradually curve. Illustratively, a gradual curving of flexible housing tube 300 may be configured to gradually curve optic fiber 310, e.g., from an optic fiber in a third curved position 530 to an optic fiber in a fourth curved position 540. In one or more embodiments, a line tangent to optic fiber distal end 311 may be parallel to a line tangent to flexible housing tube proximal end 302, e.g., when optic fiber 310 comprises an optic fiber in a fourth curved position 540. Illustratively, auto-fixing actuation control 120 and auto-fixing component 420 may be configured to temporarily fix auto-fixing actuation control 120 in a fifth fixed position within actuation control guide 210. In one or more embodiments, optic fiber 310 may comprise an optic fiber in a fourth curved position 540, e.g., when auto-fixing actuation control 120 is fixed in the fifth fixed position within actuation control guide 210.

In one or more embodiments, one or more properties of a steerable laser probe may be adjusted to attain one or more desired steerable laser probe features. Illustratively, a distance that flexible housing tube distal end 301 extends from actuation mechanism distal end 111 may be adjusted to vary an amount of actuation of auto-fixing actuation control 120 configured to curve flexible housing tube 300 to a particular curved position. In one or more embodiments, a stiffness of flexible housing tube 300 may be adjusted to vary an amount of actuation of auto-fixing actuation control 120 configured to curve flexible housing tube 300 to a particular curved position. Illustratively, a stiffness of flexible housing tube 300 may be adjusted to vary a bend radius of flexible housing tube 300. In one or more embodiments, a stiffness of flexible housing tube 300 may be adjusted to vary a radius of curvature of flexible housing tube 300, e.g., when flexible housing tube 300 is in a particular curved position.

In one or more embodiments, at least a portion of optic fiber 310 may be enclosed in an optic fiber sleeve configured to, e.g., protect optic fiber 310, vary a stiffness of optic fiber 310, vary an optical property of optic fiber 310, etc. Illustratively, an optic fiber sleeve may be configured to compress a portion of flexible housing tube 300. For example, an optic fiber sleeve may be disposed over a portion of optic fiber 310 fixed within optic fiber housing 160 and the optic fiber sleeve may be disposed over a portion of optic fiber 310 fixed to a portion of flexible housing tube 300. In one or more embodiments, an extension of auto-fixing actuation control 120 relative to actuation control guide proximal end 212 may be configured to extend flexible housing tube 300 relative to the optic fiber sleeve. Illustratively, an extension of flexible housing tube 300 relative to the optic fiber sleeve may cause the optic fiber sleeve to apply a force to a portion of flexible housing tube 300. Illustratively, an application of a force to a portion of flexible housing tube 300 may be configured to compress a portion of flexible housing tube 300 causing flexible housing tube 300 to gradually curve.

Illustratively, optic fiber 310 may comprise a buffer, a cladding disposed in the buffer, and a core disposed in the cladding. In one or more embodiments, at least a portion of optic fiber 310 may comprise a buffer configured to protect an optical property of optic fiber 310. Illustratively, at least a portion of optic fiber 310 may comprise a buffer configured to protect an optical layer of optic fiber 310, e.g., the buffer may protect an optical layer of a curved portion of optic fiber 310. In one or more embodiments, at least a portion of optic fiber 310 may comprise a polyimide buffer configured to protect an optical property of optic fiber 310. For example, at least a portion of optic fiber 310 may comprise a Kapton buffer configured to protect an optical property of optic fiber 310.

Illustratively, a steerable laser probe may be configured to indicate, e.g., to a surgeon, a direction that optic fiber 310 may curve, e.g., due to an actuation of auto-fixing actuation control 120 within actuation control guide 210. In one or more embodiments, a portion of a steerable laser probe, e.g., handle 200, may be marked in a manner configured to indicate a direction that optic fiber 310 may curve. For example, a portion of flexible housing tube 300 may comprise a mark configured to indicate a direction that optic fiber 310 may curve. Illustratively, flexible housing tube 300 may comprise a slight curve, e.g., a curve less than 7.5 degrees, when auto-fixing actuation control 120 is fully retracted relative to actuation control guide proximal end 212. For example, flexible housing tube 300 may comprise a slight curve, e.g., a curve greater than 7.5 degrees, when auto-fixing actuation control 120 is fully retracted relative to actuation control guide proximal end 212. In one or more embodiments, flexible housing tube 300 may comprise a slight curve configured to indicate a direction that optic fiber 310 may curve, e.g., due to an actuation of auto-fixing actuation control 120 within actuation control guide 210.

Figure 6A:
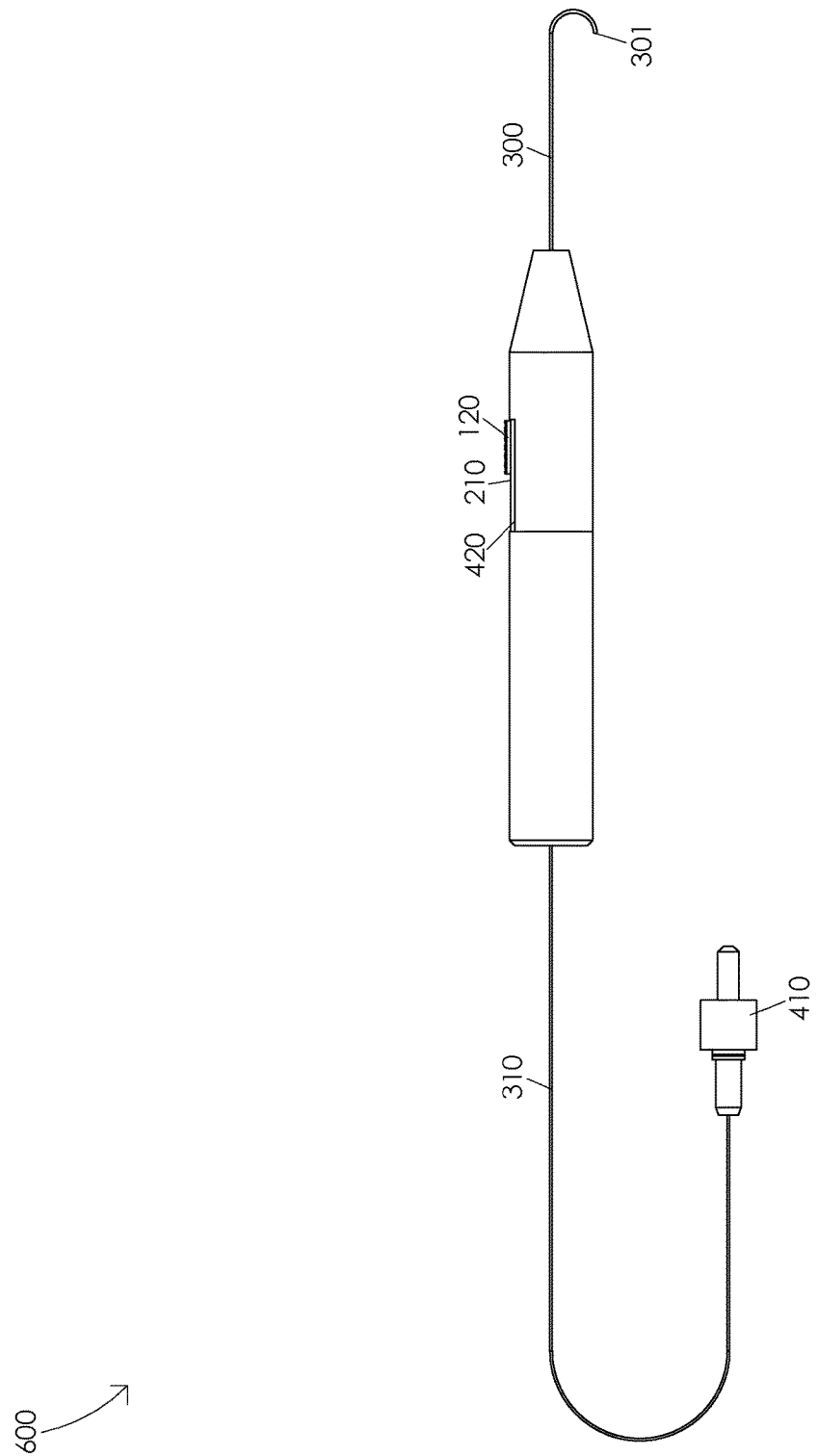
FIGS. 6A, 6B, 6C, 6D, and 6E are schematic diagrams illustrating a gradual straightening of an optic fiber.

FIGS. 6A, 6B, 6C, 6D, and 6E are schematic diagrams illustrating a gradual straightening of an optic fiber 310. FIG. 6A illustrates a fully curved optic fiber 600. In one or more embodiments, optic fiber 310 may comprise a fully curved optic fiber 600, e.g., when auto-fixing actuation control 120 is fully extended relative to actuation control guide proximal end 212. Illustratively, optic fiber 310 may comprise a fully curved optic fiber 600, e.g., when actuation mechanism 110 is fully extended relative to handle proximal end 202. In one or more embodiments, a line tangent to optic fiber distal end 311 may be parallel to a line tangent to flexible housing tube proximal end 302, e.g., when optic fiber 310 comprises a fully curved optic fiber 600.

Figure 6B:
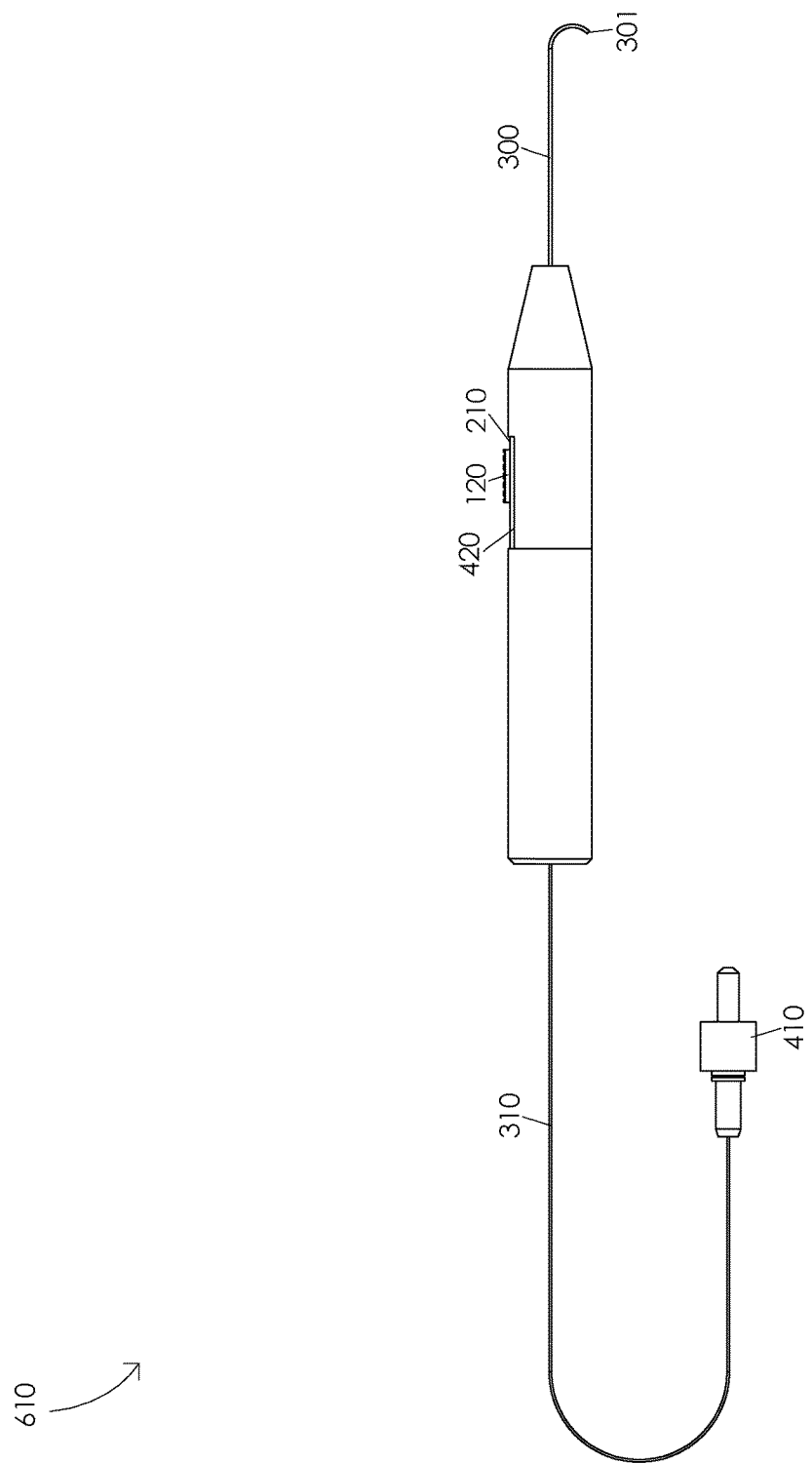

FIG. 6B illustrates an optic fiber in a first partially straightened position 610. In one or more embodiments, a retraction of auto-fixing actuation control 120 relative to actuation control guide proximal end 212 may be configured to gradually straighten optic fiber 310 from a fully curved optic fiber 600 to an optic fiber in a first partially straightened position 610. Illustratively, a retraction of auto-fixing actuation control 120 relative to actuation control guide proximal end 212 may be configured to retract actuation mechanism 110 relative to handle proximal end 202. In one or more embodiments, a retraction of actuation mechanism 110 relative to handle proximal end 202 may be configured to retract flexible housing tube 300 relative to optic fiber 310. Illustratively, a portion of optic fiber 310, e.g., a portion of optic fiber 310 fixed to flexible housing tube 300, may be configured to facilitate a retraction of flexible housing tube 300 relative to optic fiber 310. In one or more embodiments, a portion of optic fiber 310 may be configured to reduce a force applied to a portion of flexible housing tube 300, e.g., due to a retraction of flexible housing tube 300 relative to optic fiber 310. Illustratively, a reduction of a force applied to a portion of flexible housing tube 300 may be configured to decompress a portion of flexible housing tube 300. In one or more embodiments, a decompression of a portion of flexible housing tube 300 may cause flexible housing tube 300 to gradually straighten. Illustratively, a gradual straightening of flexible housing tube 300 may be configured to gradually straighten optic fiber 310, e.g., from a fully curved optic fiber 600 to an optic fiber in a first partially straightened position 610. In one or more embodiments, a line tangent to optic fiber distal end 311 may intersect a line tangent to flexible housing tube proximal end 302 at a first partially straightened angle, e.g., when optic fiber 310 comprises an optic fiber in a first partially straightened position 610. Illustratively, the first partially straightened angle may comprise any angle less than 180 degrees. For example, the first partially straightened angle may comprise a 135 degree angle.

Figure 6C:
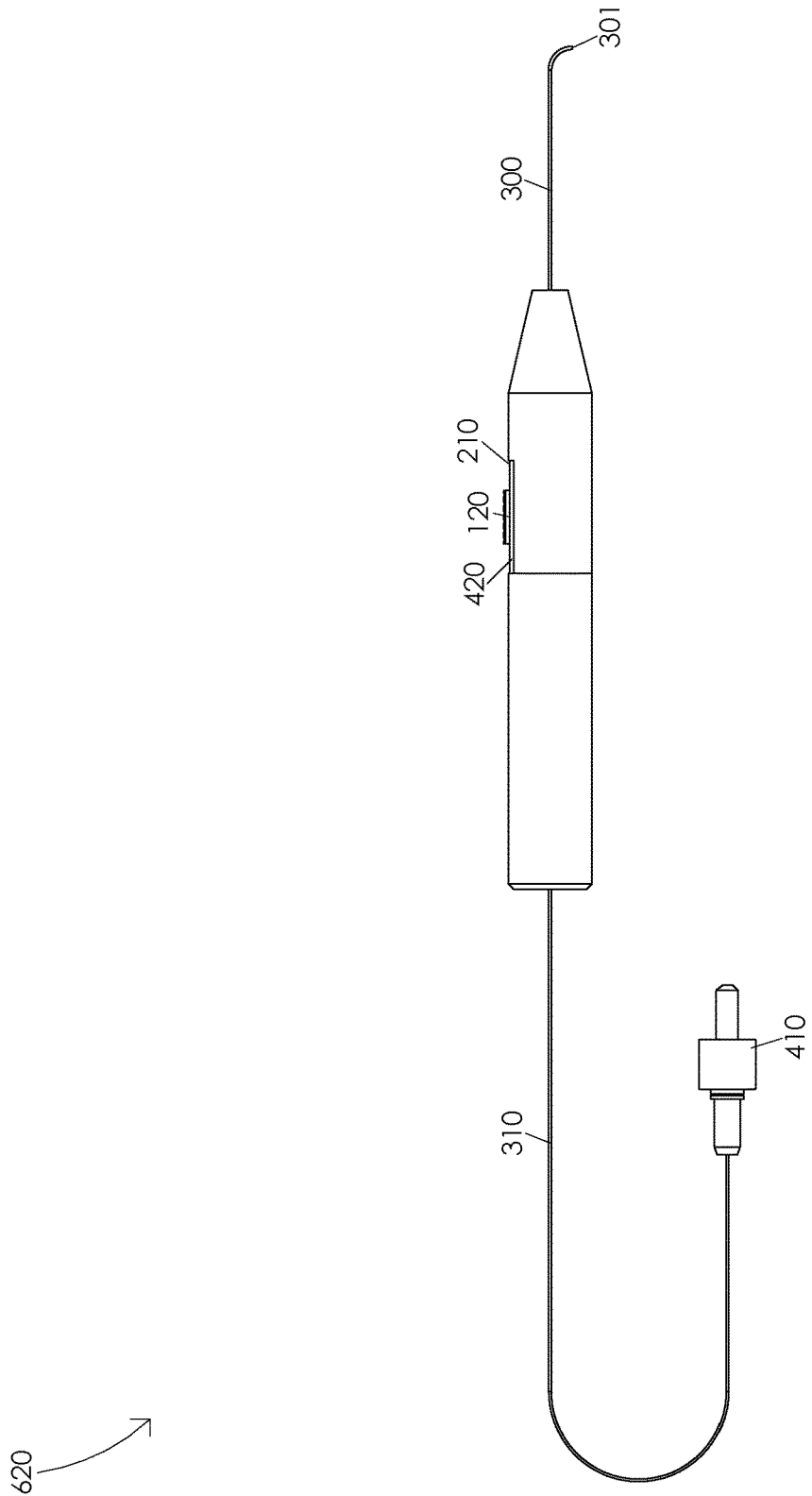

FIG. 6C illustrates an optic fiber in a second partially straightened position 620. In one or more embodiments, a retraction of auto-fixing actuation control 120 relative to actuation control guide proximal end 212 may be configured to gradually straighten optic fiber 310 from an optic fiber in a first partially straightened position 610 to an optic fiber in a second partially straightened position 620. Illustratively, a retraction of auto-fixing actuation control 120 relative to actuation control guide proximal end 212 may be configured to retract actuation mechanism 110 relative to handle proximal end 202. In one or more embodiments, a retraction of actuation mechanism 110 relative to handle proximal end 202 may be configured to retract flexible housing tube 300 relative to optic fiber 310. Illustratively, a portion of optic fiber 310, e.g., a portion of optic fiber 310 fixed to flexible housing tube 300, may be configured to facilitate a retraction of flexible housing tube 300 relative to optic fiber 310. In one or more embodiments, a portion of optic fiber 310 may be configured to reduce a force applied to a portion of flexible housing tube 300, e.g., due to a retraction of flexible housing tube 300 relative to optic fiber 310. Illustratively, a reduction of a force applied to a portion of flexible housing tube 300 may be configured to decompress a portion of flexible housing tube 300. In one or more embodiments, a decompression of a portion of flexible housing tube 300 may cause flexible housing tube 300 to gradually straighten. Illustratively, a gradual straightening of flexible housing tube 300 may be configured to gradually straighten optic fiber 310, e.g., from an optic fiber in a first partially straightened position 610 to an optic fiber in a second partially straightened position 620. In one or more embodiments, a line tangent to optic fiber distal end 311 may intersect a line tangent to flexible housing tube proximal end 302 at a second partially straightened angle, e.g., when optic fiber 310 comprises an optic fiber in a second partially straightened position 620. Illustratively, the second partially straightened angle may comprise any angle less than the first partially straightened angle. For example, the second partially straightened angle may comprise a 90 degree angle.

Figure 6D:
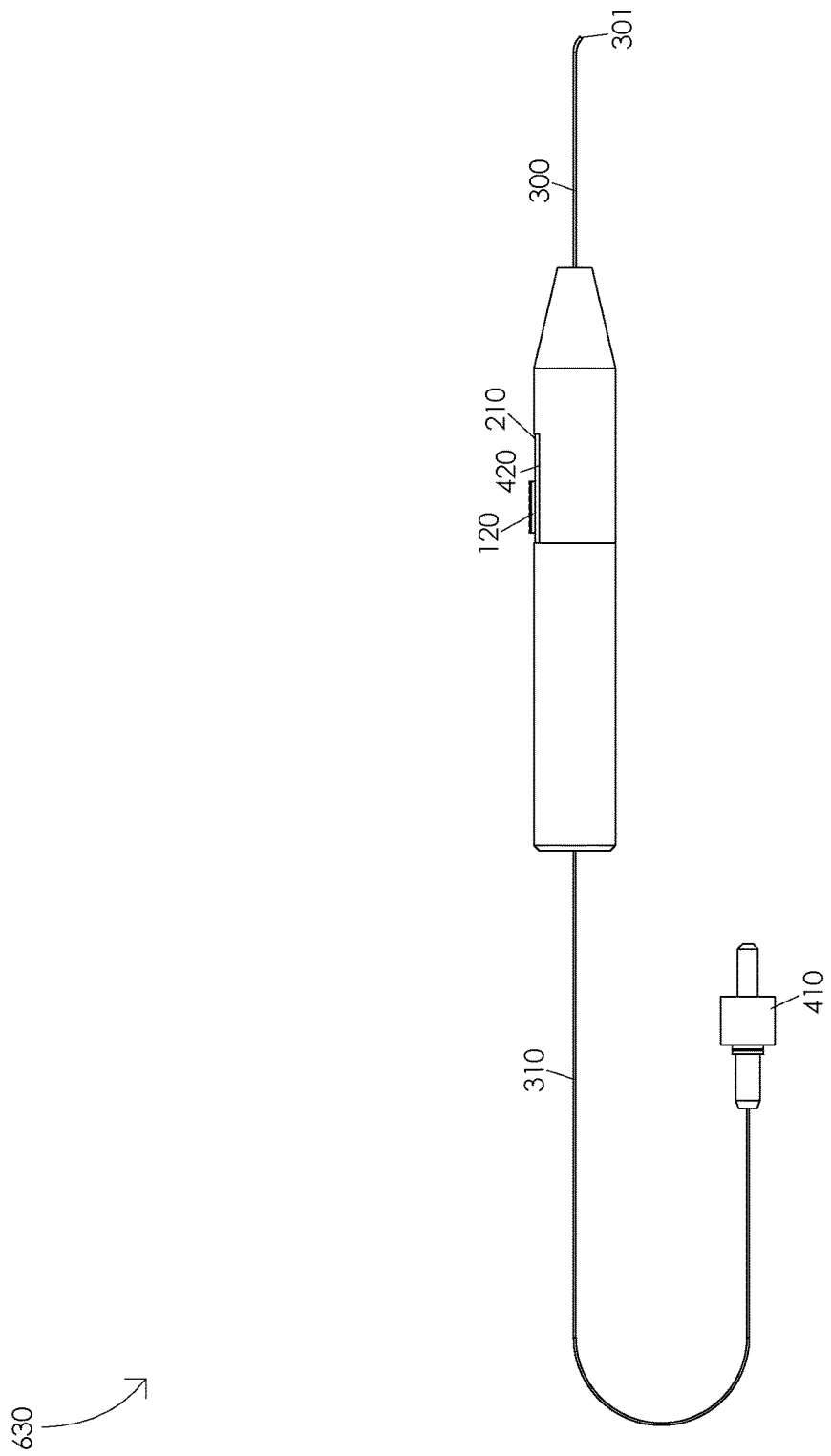

FIG. 6D illustrates an optic fiber in a third partially straightened position 630. In one or more embodiments, a retraction of auto-fixing actuation control 120 relative to actuation control guide proximal end 212 may be configured to gradually straighten optic fiber 310 from an optic fiber in a second partially straightened position 620 to an optic fiber in a third partially straightened position 630. Illustratively, a retraction of auto-fixing actuation control 120 relative to actuation control guide proximal end 212 may be configured to retract actuation mechanism 110 relative to handle proximal end 202. In one or more embodiments, a retraction of actuation mechanism 110 relative to handle proximal end 202 may be configured to retract flexible housing tube 300 relative to optic fiber 310. Illustratively, a portion of optic fiber 310, e.g., a portion of optic fiber 310 fixed to flexible housing tube 300, may be configured to facilitate a retraction of flexible housing tube 300 relative to optic fiber 310. In one or more embodiments, a portion of optic fiber 310 may be configured to reduce a force applied to a portion of flexible housing tube 300, e.g., due to a retraction of flexible housing tube 300 relative to optic fiber 310. Illustratively, a reduction of a force applied to a portion of flexible housing tube 300 may be configured to decompress a portion of flexible housing tube 300. In one or more embodiments, a decompression of a portion of flexible housing tube 300 may cause flexible housing tube 300 to gradually straighten. Illustratively, a gradual straightening of flexible housing tube 300 may be configured to gradually straighten optic fiber 310, e.g., from an optic fiber in a second partially straightened position 620 to an optic fiber in a third partially straightened position 630. In one or more embodiments, a line tangent to optic fiber distal end 311 may intersect a line tangent to flexible housing tube proximal end 302 at a third partially straightened angle, e.g., when optic fiber 310 comprises an optic fiber in a third partially straightened position 630. Illustratively, the third partially straightened angle may comprise any angle less than the second partially straightened angle. For example, the third partially straightened angle may comprise a 45 degree angle.

Figure 6E:
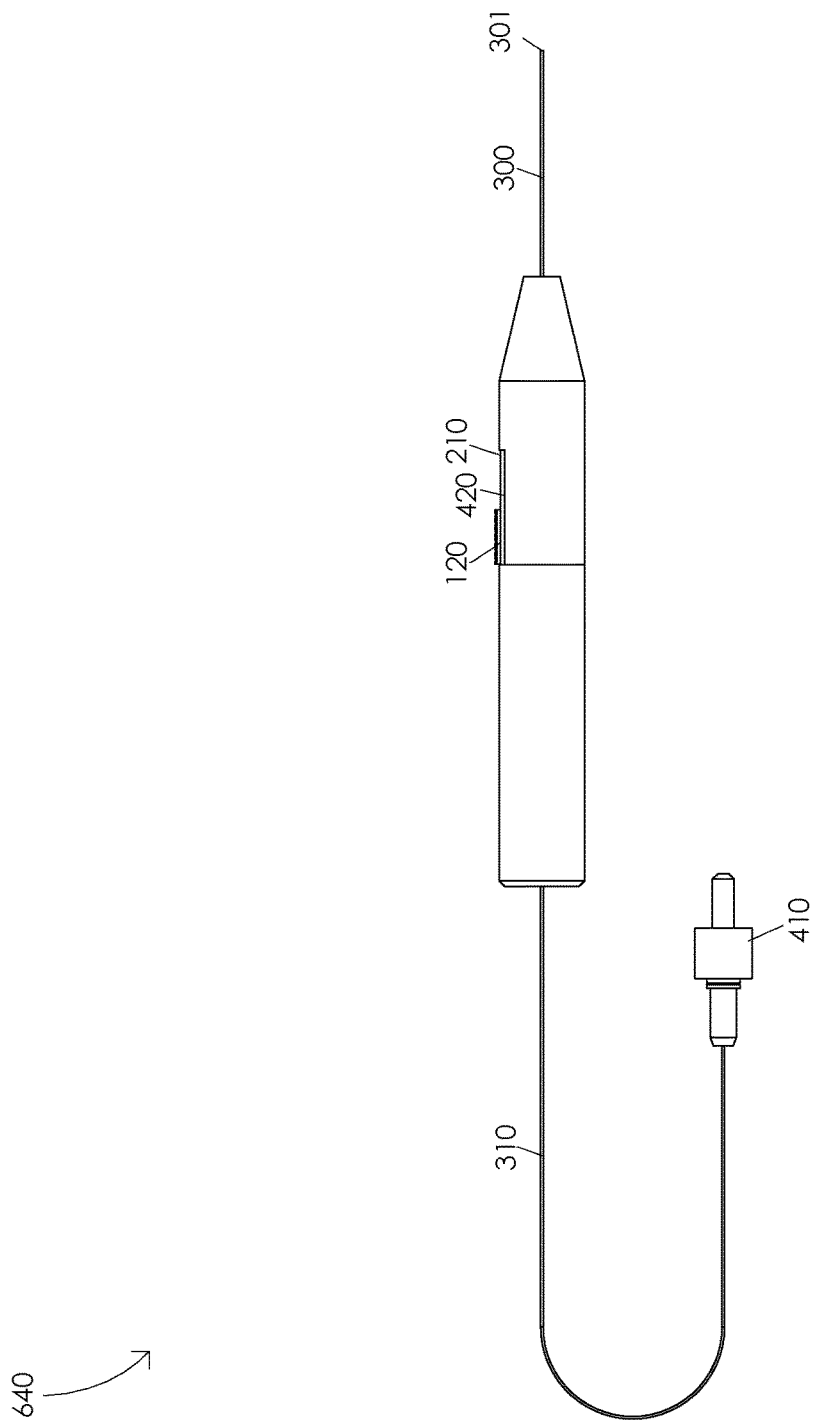

FIG. 6E illustrates an optic fiber in a fully straightened position 640. In one or more embodiments, a retraction of auto-fixing actuation control 120 relative to actuation control guide proximal end 212 may be configured to gradually straighten optic fiber 310 from an optic fiber in a third partially straightened position 630 to an optic fiber in a fully straightened position 640. Illustratively, a retraction of auto-fixing actuation control 120 relative to actuation control guide proximal end 212 may be configured to retract actuation mechanism 110 relative to handle proximal end 202. In one or more embodiments, a retraction of actuation mechanism 110 relative to handle proximal end 202 may be configured to retract flexible housing tube 300 relative to optic fiber 310. Illustratively, a portion of optic fiber 310, e.g., a portion of optic fiber 310 fixed to flexible housing tube 300, may be configured to facilitate a retraction of flexible housing tube 300 relative to optic fiber 310. In one or more embodiments, a portion of optic fiber 310 may be configured to reduce a force applied to a portion of flexible housing tube 300, e.g., due to a retraction of flexible housing tube 300 relative to optic fiber 310. Illustratively, a reduction of a force applied to a portion of flexible housing tube 300 may be configured to decompress a portion of flexible housing tube 300. In one or more embodiments, a decompression of a portion of flexible housing tube 300 may cause flexible housing tube 300 to gradually straighten. Illustratively, a gradual straightening of flexible housing tube 300 may be configured to gradually straighten optic fiber 310, e.g., from an optic fiber in a third partially straightened position 630 to an optic fiber in a fully straightened position 640. In one or more embodiments, a line tangent to optic fiber distal end 311 may be parallel to a line tangent to flexible housing tube proximal end 302, e.g., when optic fiber 310 comprises an optic fiber in a fully straightened position 640.

Illustratively, a surgeon may aim optic fiber distal end 311 at any of a plurality of targets within an eye, e.g., to perform a photocoagulation procedure, to illuminate a surgical target site, etc. In one or more embodiments, a surgeon may aim optic fiber distal end 311 at any target within a particular transverse plane of the inner eye by, e.g., rotating handle 200 to orient flexible housing tube 300 in an orientation configured to cause a curvature of flexible housing tube 300 within the particular transverse plane of the inner eye and varying an amount of actuation of auto-fixing actuation control 120 within actuation control guide 210. Illustratively, a surgeon may aim optic fiber distal end 311 at any target within a particular sagittal plane of the inner eye by, e.g., rotating handle 200 to orient flexible housing tube 300 in an orientation configured to cause a curvature of flexible housing tube 300 within the particular sagittal plane of the inner eye and varying an amount of actuation of auto-fixing actuation control 120 within actuation control guide 210. In one or more embodiments, a surgeon may aim optic fiber distal end 311 at any target within a particular frontal plane of the inner eye by, e.g., varying an amount of actuation of auto-fixing actuation control 120 within actuation control guide 210 to orient a line tangent to optic fiber distal end 311 wherein the line tangent to optic fiber distal end 311 is within the particular frontal plane of the inner eye and rotating handle 200. Illustratively, a surgeon may aim optic fiber distal end 311 at any target located outside of the particular transverse plane, the particular sagittal plane, and the particular frontal plane of the inner eye, e.g., by varying a rotational orientation of handle 200 and varying an amount of actuation of auto-fixing actuation control 120 within actuation control guide 210. In one or more embodiments, a surgeon may aim optic fiber distal end 311 at any target of a plurality of targets within an eye, e.g., without increasing a length of a portion of a steerable laser probe within the eye. Illustratively, a surgeon may aim optic fiber distal end 311 at any target of a plurality of targets within an eye, e.g., without decreasing a length of a portion of a steerable laser probe within the eye.

FIGS. 7A and 7B are schematic diagrams illustrating an exploded view of a handle assembly 700. FIG. 7A illustrates a side view of a handle assembly 700. Illustratively, a handle assembly 700 may comprise a handle end cap 705 having a handle end cap distal end 706 and a handle end cap proximal end 707, an actuation mechanism 710 having an actuation mechanism distal end 711 and an actuation mechanism proximal end 712, an auto-fixing actuation control 720 having an auto-fixing actuation control distal end 721 and an auto-fixing actuation control proximal end 722, a handle base 730 having a handle base distal end 731 and a handle base proximal end 732, a handle end cap interface 735, an auto-fixing component housing 740, and a handle base channel 745.

FIG. 7B illustrates a cross-sectional view of a handle assembly 700. In one or more embodiments, a handle assembly 700 may comprise an actuation mechanism guide 750, a handle base housing 755, a handle base interface 756, an cable housing 760, an inner bore 770, a flexible housing tube housing 775, a distal chamber 780, and a flexible housing tube guide 790. Illustratively, handle end cap 705, actuation mechanism 710, auto-fixing actuation control 720, and handle base 730 may be manufactured from any suitable material, e.g., polymers, metals, metal alloys, etc., or from any combination of suitable materials.

FIGS. 8A and 8B are schematic diagrams illustrating a handle 800. FIG. 8A illustrates a side view of a handle 800. Illustratively, handle 800 may comprise a handle distal end 801 and a handle proximal end 802. In one or more embodiments, handle 800 may comprise an actuation control guide 810 having an actuation control guide distal end 811 and an actuation control guide proximal end 812.

Illustratively, handle 800 may be manufactured from any suitable material, e.g., polymers, metals, metal alloys, etc., or from any combination of suitable materials.

FIG. 8B illustrates a cross-sectional view of a handle 800. Illustratively, actuation mechanism 710 may be disposed within handle end cap 705 and handle base 730. In one or more embodiments, a portion of handle base 730 may be disposed within handle base housing 755, e.g., handle base proximal end 732 may be disposed within handle base housing 755. Illustratively, handle base 730 may be disposed within handle base housing 755, e.g., handle base proximal end 732 may interface with handle base interface 756. For example, handle base 730 may be disposed within end cap 705 wherein end cap distal end 706 may interface with handle end cap interface 735. In one or more embodiments, handle base 730 may be fixed within handle base housing 755, e.g., by an adhesive or any suitable fixation means. For example, handle base 730 may be fixed within handle base housing 755 by a press fit, a setscrew, a weld, etc. Illustratively, handle base 730 and handle end cap 705 may be manufactured as a single unit.

In one or more embodiments, auto-fixing actuation control 720 may be disposed within actuation control guide 810. For example, auto-fixing actuation control 720 may be disposed within actuation control guide 810 wherein auto-fixing actuation control 720 is adjacent to auto-fixing component housing 740. Illustratively, actuation control guide 810 may comprise a portion of handle base channel 745. In one or more embodiments, handle end cap distal end 706 may comprise actuation control guide proximal end 812. Illustratively, auto-fixing actuation control 720 may be configured to actuate within actuation control guide 810. In one or more embodiments, actuation mechanism 710 may be configured to actuate within actuation mechanism guide 750. Illustratively, an actuation of auto-fixing actuation control 720 may be configured to actuate actuation mechanism 710. In one or more embodiments, an actuation of auto-fixing actuation control 720 within actuation control guide 810 may be configured to actuate actuation mechanism 710 within actuation mechanism guide 750.

Illustratively, an actuation of auto-fixing actuation control 720 within actuation control guide 810, e.g., away from actuation control guide proximal end 812 and towards actuation control guide distal end 811, may be configured to actuate actuation mechanism 710 within actuation mechanism guide 750, e.g., away from handle proximal end 802 and towards handle distal end 801. In one or more embodiments, an extension of auto-fixing actuation control 720 relative to actuation control guide proximal end 812 may be configured to extend actuation mechanism 710 relative to handle proximal end 802. Illustratively, an extension of actuation mechanism 710 relative to handle proximal end 802 may be configured to extend flexible housing tube housing 775 relative to handle proximal end 802.

In one or more embodiments, an actuation of auto-fixing actuation control 720 within actuation control guide 810, e.g., away from actuation control guide distal end 811 and towards actuation control guide proximal end 812 may be configured to actuate actuation mechanism 710 within actuation mechanism guide 750, e.g., towards handle proximal end 802 and away from handle distal end 801. Illustratively, a retraction of auto-fixing actuation control 720 relative to actuation control guide proximal end 812 may be configured to retract actuation mechanism 710 relative to handle proximal end 802. In one or more embodiments, a retraction of actuation mechanism 710 relative to handle proximal end 802 may be configured to retract flexible housing tube housing 775 relative to handle proximal end 802.

Figure 9:
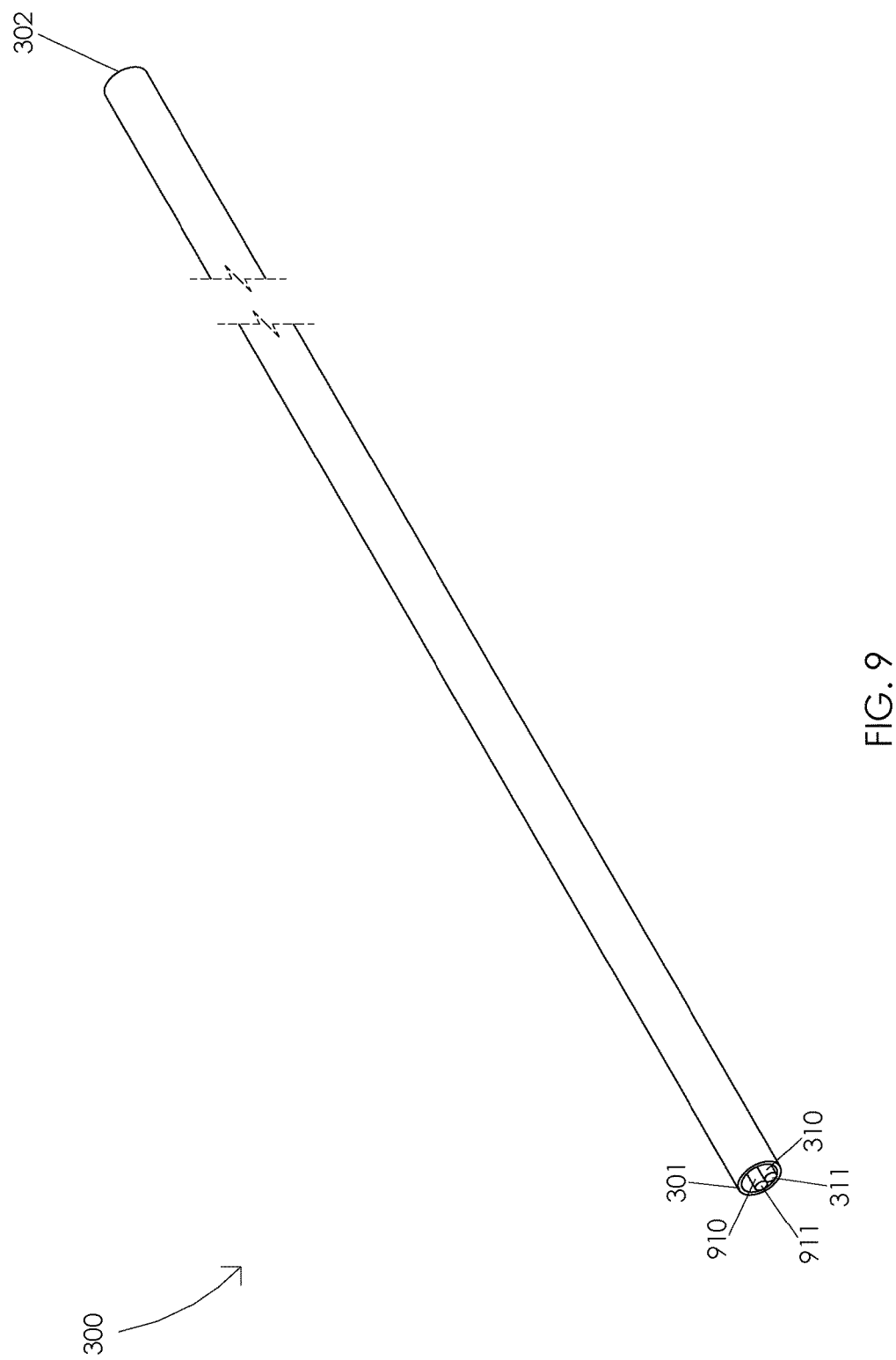
FIG. 9 is a schematic diagram illustrating a flexible housing tube.

FIG. 9 is a schematic diagram illustrating a flexible housing tube 300. Illustratively, an optic fiber 310 may be disposed within flexible housing tube 300. In one or more embodiments, optic fiber 310 may comprise an optic fiber distal end 311 and an optic fiber proximal end 312. Illustratively, optic fiber 310 may be configured to transmit light, e.g., laser light, illumination light, etc. In one or more embodiments, optic fiber 310 may be disposed within flexible housing tube 300 wherein optic fiber distal end 311 may be adjacent to flexible housing tube distal end 301. Illustratively, a portion of optic fiber 310 may be fixed to an inner portion of flexible housing tube 300, e.g., by an adhesive or any suitable fixation means. Illustratively, a cable 910 may be disposed in flexible housing tube 300. In one or more embodiments, cable 910 may comprise a cable distal end 911 and a cable proximal end 912. In one or more embodiments, cable 910 may be disposed within flexible housing tube 300 wherein cable distal end 911 may be adjacent to flexible housing tube distal end 301. Illustratively, a portion of cable 910 may be fixed to a portion of flexible housing tube 300, e.g., by an adhesive or any suitable fixation means. For example, cable 810 may be fixed to a portion of flexible housing tube 300 by a weld, a mechanical means, a tie, etc.

Figure 10:
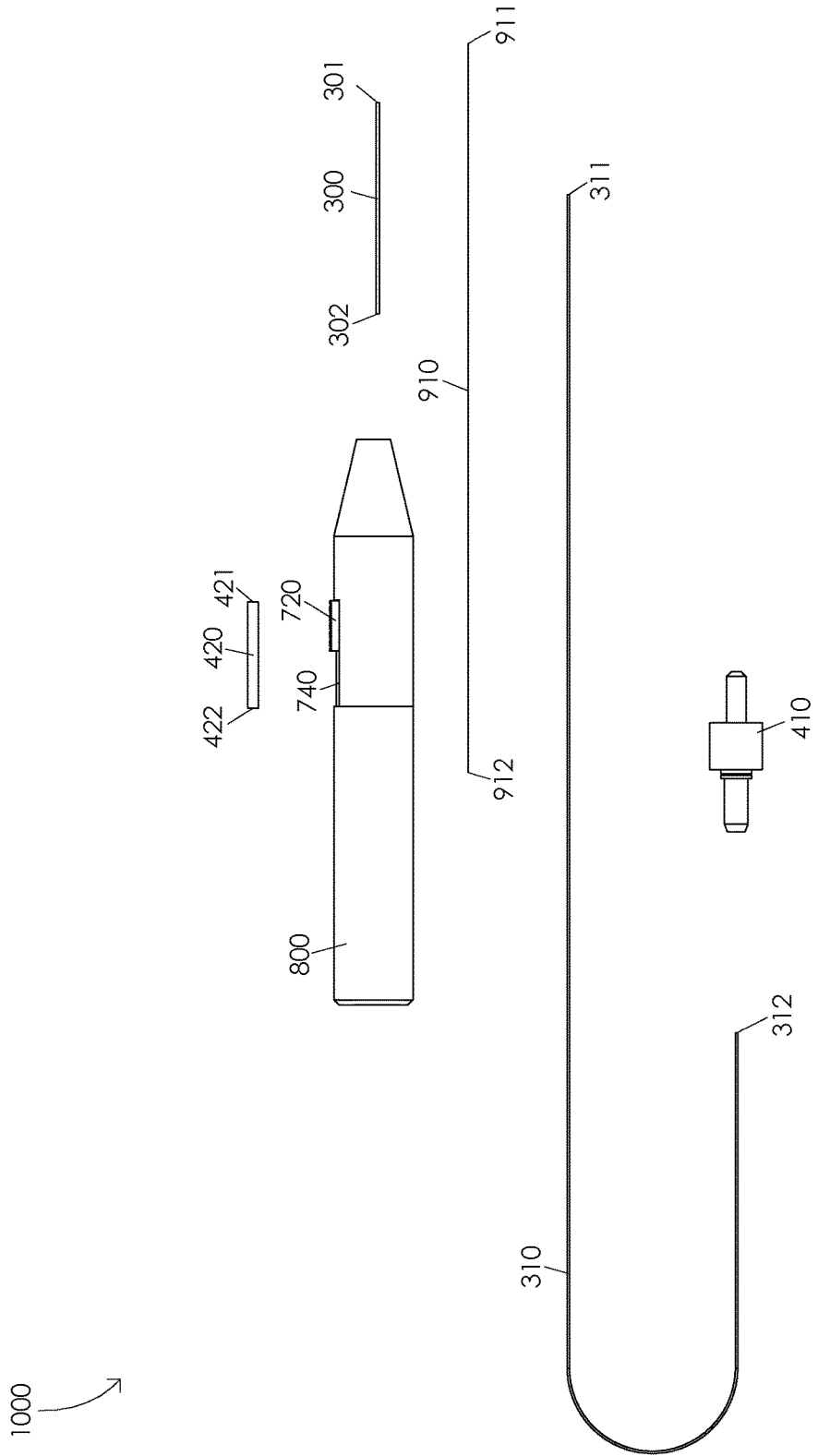
FIG. 10 is a schematic diagram illustrating an exploded view of a steerable laser probe assembly.

FIG. 10 is a schematic diagram illustrating an exploded view of a steerable laser probe assembly 1000. In one or more embodiments, a steerable laser probe assembly 1000 may comprise a handle 800, a flexible housing tube 300 having a flexible housing tube distal end 301 and a flexible housing tube proximal end 302, an optic fiber 310 having an optic fiber distal end 311 and an optic fiber proximal end 312, a cable 910 having a cable distal end 911 and a cable proximal end 912, an auto-fixing component 420 having an auto-fixing component distal end 421 and an auto-fixing component proximal end 422, and a light source interface 410. Illustratively, light source interface 410 may be configured to interface with optic fiber 310, e.g., at optic fiber proximal end 312. In one or more embodiments, light source interface 410 may comprise a standard light source connector, e.g., an SMA connector.

Illustratively, flexible housing tube 300 may be disposed within flexible housing tube housing 775, actuation mechanism guide 750, and flexible housing tube guide 790. In one or more embodiments, a portion of flexible housing tube 300 may be fixed within flexible housing tube housing 775, e.g., flexible housing tube proximal end 302 may be fixed within flexible housing tube housing 775. Illustratively, a portion of flexible housing tube 300 may be fixed within flexible housing tube housing 775, e.g., by an adhesive or any suitable fixation means. For example, a portion of flexible housing tube 300 may be fixed within flexible housing tube housing 775 by a press fit, a set screw, etc. In one or more embodiments, flexible housing tube 300 may be fixed within flexible housing tube housing 775 wherein flexible housing tube distal end 301 extends from handle distal end 801.

Illustratively, optic fiber 310 may be disposed within cable housing 760, actuation mechanism guide 750, inner bore 770, flexible housing tube 300, and flexible housing tube guide 790. In one or more embodiments, optic fiber 310 may be disposed within flexible housing tube 300 wherein optic fiber distal end 311 may be adjacent to flexible housing tube distal end 301. Illustratively, a portion of optic fiber 310 may be fixed within flexible housing tube 300, e.g., by an adhesive or any suitable fixation means. In one or more embodiments, cable 910 may be disposed within cable housing 760, actuation mechanism guide 750, inner bore 770, flexible housing tube 300, and flexible housing tube guide 790. Illustratively, cable 910 may be disposed within flexible housing tube 300 wherein cable distal end 911 may be adjacent to flexible housing tube distal end 301. In one or more embodiments, a portion of cable 910 may be fixed to a portion of flexible housing tube 300, e.g., by an adhesive or any suitable fixation means. For example, cable 910 may be fixed to a portion of flexible housing tube 300 by a weld, a tie, a setscrew, etc. Illustratively, a portion of cable 910 may be fixed within cable housing 760, e.g., cable proximal end 912 may be fixed within cable housing 760. In one or more embodiments, a portion of cable 910 may be fixed within cable housing 760, e.g., by an adhesive or any suitable fixation means. For example, cable 910 may be fixed within cable housing 760 by a weld, a tie, a setscrew, etc. Illustratively, a first portion of cable 910 may be fixed within cable housing 760 and a second portion of cable 910 may be fixed to a portion of flexible housing tube 300.

In one or more embodiments, an actuation of auto-fixing actuation control 720 within actuation control guide 810, e.g., towards actuation control guide distal end 811 and away from actuation control guide proximal end 812, may be configured to actuate actuation mechanism 710 within actuation mechanism guide 750, e.g., towards handle distal end 801 and away from handle proximal end 802. Illustratively, an extension of auto-fixing actuation control 720 relative to actuation control guide proximal end 812 may be configured to extend actuation mechanism 710 relative to handle proximal end 802. In one or more embodiments, an extension of actuation mechanism 710 relative to handle proximal end 802 may be configured to extend flexible housing tube housing 775 relative to handle proximal end 802. Illustratively, an extension of flexible housing tube housing 775 relative to handle proximal end 802 may be configured to extend flexible housing tube 300 relative to handle proximal end 802. In one or more embodiments, an extension of flexible housing tube 300 relative to handle proximal end 802 may be configured to extend flexible housing tube 300 relative to cable 910. Illustratively, a portion of cable 910, e.g., a portion of cable 910 fixed to flexible housing tube 300, may be configured to resist an extension of flexible housing tube 300 relative to cable 910. In one or more embodiments, a portion of cable 910 may be configured to prevent flexible housing tube 300 from extending relative to cable 910. Illustratively, an extension of flexible housing tube 300 relative to cable 910 may be configured to apply a force to a portion of flexible housing tube 300. In one or more embodiments, an application of a force to a portion of flexible housing tube 300 may be configured to compress a portion of flexible housing tube 300. Illustratively, a compression of a portion of flexible housing tube 300 may be configured to cause flexible housing tube 300 to gradually curve. In one or more embodiments, a gradual curving of flexible housing tube 300 may be configured to gradually curve optic fiber 310.

In one or more embodiments, an actuation of auto-fixing actuation control 720 within actuation control guide 810, e.g., towards actuation control guide proximal end 812 and away from actuation control guide distal end 811, may be configured to actuate actuation mechanism 710 within actuation mechanism guide 750, e.g., towards handle proximal end 802 and away from handle distal end 801. Illustratively, a retraction of auto-fixing actuation control 720 relative to actuation control guide proximal end 812 may be configured to retract actuation mechanism 710 relative to handle proximal end 802. In one or more embodiments, a retraction of actuation mechanism 710 relative to handle proximal end 802 may be configured to retract flexible housing tube housing 775 relative to handle proximal end 802. Illustratively, a retraction of flexible housing tube housing 775 relative to handle proximal end 802 may be configured to retract flexible housing tube 300 relative to handle proximal end 802. In one or more embodiments, a retraction of flexible housing tube 300 relative to handle proximal end 802 may be configured to retract flexible housing tube 300 relative to cable 910. Illustratively, a portion of cable 910, e.g., a portion of cable 910 fixed to flexible housing tube 300, may be configured to facilitate a retraction of flexible housing tube 300 relative to cable 910. In one or more embodiments, a retraction of flexible housing tube 300 relative to cable 910 may be configured to reduce a force applied to a portion of flexible housing tube 300. Illustratively, a reduction of a force applied to a portion of flexible housing tube 300 may be configured to decompress a portion of flexible housing tube 300. In one or more embodiments, a decompression of a portion of flexible housing tube 300 may be configured to cause flexible housing tube 300 to gradually straighten. Illustratively, a gradual straightening of flexible housing tube 300 may be configured to gradually straighten optic fiber 310.

In one or more embodiments, auto-fixing component 420 may be disposed within auto-fixing component housing 740. Illustratively, auto-fixing component 420 may be fixed within auto-fixing component housing 740, e.g., by an adhesive or any suitable fixation means. In one or more embodiments, auto-fixing component 420 may be disposed within auto-fixing component housing 740 wherein a portion of auto-fixing component 420 may be adjacent to a portion of auto-fixing actuation control 720. Illustratively, auto-fixing component 420 may be configured to produce a magnetic field, e.g., auto-fixing component 420 may comprise a permanent magnet. In one or more embodiments, auto-fixing component 420 may comprise a ferromagnetic material, e.g., auto-fixing component 420 may comprise a ferrimagnetic material. Illustratively, auto-fixing actuation control 720 may be configured to produce a magnetic field, e.g., auto-fixing actuation control 720 may comprise a permanent magnetic. In one or more embodiments, auto-fixing actuation control 720 may comprise a ferromagnetic material, e.g., auto-fixing actuation control 720 may comprise a ferrimagnetic material. Illustratively, auto-fixing component 420 may be configured to temporarily fix auto-fixing actuation control 720 in a position within actuation control guide 810, e.g., a magnetic force attracting auto-fixing actuation control 720 to auto-fixing component 420 may be configured to hold auto-fixing actuation control 720 fixed in a position within actuation control guide 810. In one or more embodiments, auto-fixing actuation control 720 may be configured to temporarily fix auto-fixing actuation control 720 in a position within actuation control guide 810, e.g., a magnetic force attracting auto-fixing component 420 to auto-fixing actuation control 720 may be configured to temporarily hold auto-fixing actuation control 720 fixed in a position within actuation control guide 810. Illustratively, both auto-fixing component 420 and auto-fixing actuation control 720 may be configured to temporarily fix auto-fixing actuation control 720 in a position within actuation control guide 210, e.g., auto-fixing component 420 and auto-fixing actuation control 720 may both comprise permanent magnets having poles oriented to attract auto-fixing component 420 to auto-fixing actuation control 720 and to attract auto-fixing actuation control 720 to auto-fixing component 420.

In one or more embodiments, a surgeon may actuate auto-fixing actuation control 720 within actuation control guide 810, e.g., by applying a force to a portion of auto-fixing actuation control 720 until auto-fixing actuation control 720 is in a first desired position within actuation control guide 810. Illustratively, the surgeon may then remove the force applied to auto-fixing actuation control 720 and perform a portion of a surgical procedure, e.g., auto-fixing actuation control 720 and auto-fixing component 420 may be configured to temporarily fix auto-fixing actuation control 720 in the first desired position within actuation control guide 810. In one or more embodiments, the surgeon may actuate auto-fixing actuation control 720 within actuation control guide 810, e.g., by applying a force to a portion of auto-fixing actuation control 720 until auto-fixing actuation control 720 is in a second desired position within actuation control guide 810. Illustratively, the surgeon may then remove the force applied to auto-fixing actuation control 720 and perform a portion of a surgical procedure, e.g., auto-fixing actuation control 720 and auto-fixing component 420 may be configured to temporarily fix auto-fixing actuation control 720 in the second desired position within actuation control guide 810. In one or more embodiments, the surgeon may actuate auto-fixing actuation control 720 within actuation control guide 810, e.g., by applying a force to a portion of auto-fixing actuation control 720 until auto-fixing actuation control 720 is in a third desired position within actuation control guide 810. Illustratively, the surgeon may then remove the force applied to auto-fixing actuation control 720 and perform a portion of a surgical procedure, e.g., auto-fixing actuation control 720 and auto-fixing component 420 may be configured to temporarily fix auto-fixing actuation control 720 in the third desired position within actuation control guide 810. In one or more embodiments, auto-fixing actuation control 720 and auto-fixing component 420 may be configured to temporarily fix auto-fixing actuation control 720 in any desired position within actuation control guide 810.

Figure 11A:
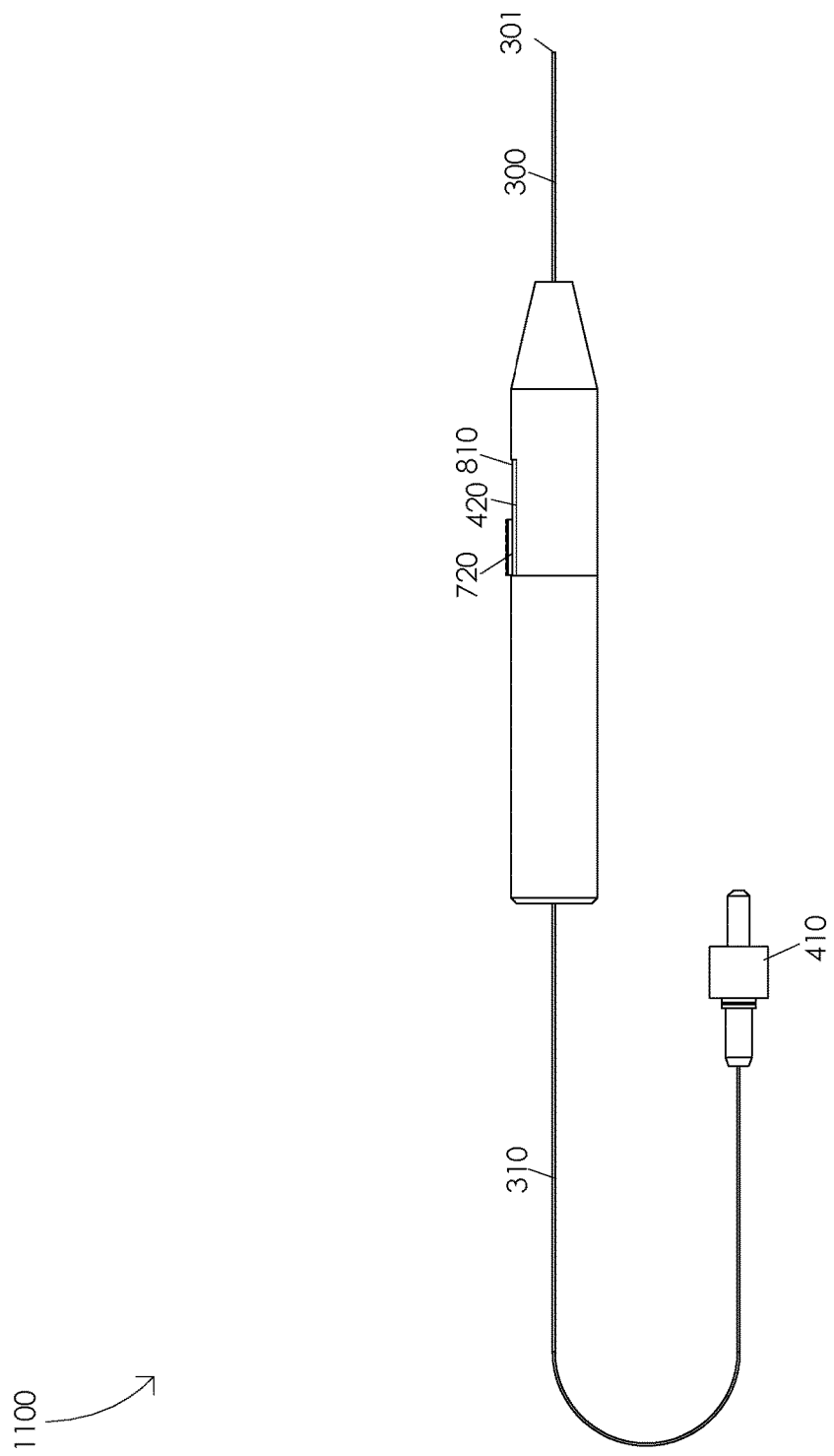

FIGS. 11A, 11B, 11C, 11D, and 11E are schematic diagrams illustrating a gradual curving of an optic fiber 310. FIG. 11A illustrates a straight optic fiber 1100. In one or more embodiments, optic fiber 310 may comprise a straight optic fiber 1100, e.g., when flexible housing tube 300 is fully retracted relative to cable 910. Illustratively, optic fiber 310 may comprise a straight optic fiber 1100, e.g., when auto-fixing actuation control 720 is fully retracted relative to actuation control guide proximal end 812. In one or more embodiments, optic fiber 310 may comprise a straight optic fiber 1100, e.g., when actuation mechanism 710 is fully retracted relative to handle proximal end 802. Illustratively, a line tangent to optic fiber distal end 311 may be parallel to a line tangent to flexible housing tube proximal end 302, e.g., when optic fiber 310 comprises a straight optic fiber 1100. In one or more embodiments, auto-fixing actuation control 720 and auto-fixing component 420 may be configured to temporarily fix auto-fixing actuation control 720 in a first fixed position within actuation control guide 810. Illustratively, optic fiber 310 may comprise a straight optic fiber 1100, e.g., when auto-fixing actuation control 720 is fixed in the first fixed position within actuation control guide 810.

Figure 11B:
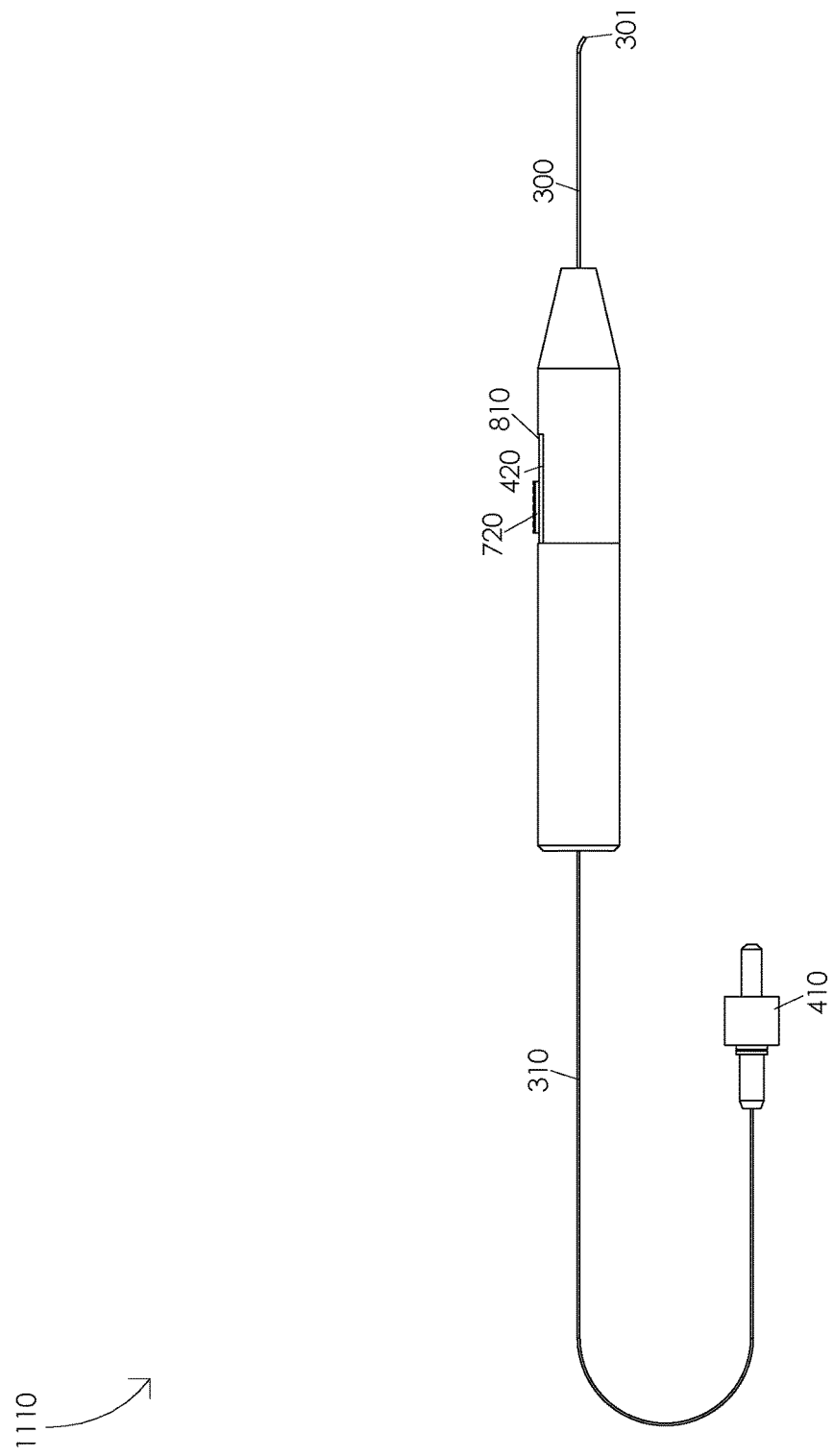

FIG. 11B illustrates an optic fiber in a first curved position 1110. In one or more embodiments, an extension of auto-fixing actuation control 720 relative to actuation control guide proximal end 812 may be configured to gradually curve optic fiber 310 from a straight optic fiber 1100 to an optic fiber in a first curved position 1110. Illustratively, an extension of auto-fixing actuation control 720 relative to actuation control guide proximal end 812 may be configured to extend actuation mechanism 710 relative to handle proximal end 802. In one or more embodiments, an extension of actuation mechanism 710 relative to handle proximal end 802 may be configured to extend flexible housing tube 300 relative to cable 910. Illustratively, a portion of cable 910, e.g., a portion of cable 910 fixed to flexible housing tube 300, may be configured to resist an extension of flexible housing tube 300 relative to cable 910. In one or more embodiments, a portion of cable 910 may be configured to apply a force to a portion of flexible housing tube 300, e.g., to resist an extension of flexible housing tube 300 relative to cable 910. Illustratively, an application of a force to a portion of flexible housing tube 300 may be configured to compress a portion of flexible housing tube 300. In one or more embodiments, a compression of a portion of flexible housing tube 300 may cause flexible housing tube 300 to gradually curve. Illustratively, a gradual curving of flexible housing tube 300 may be configured to gradually curve optic fiber 310, e.g., from a straight optic fiber 1100 to an optic fiber in a first curved position 1110. In one or more embodiments, a line tangent to optic fiber distal end 311 may intersect a line tangent to flexible housing tube proximal end 302 at a first angle, e.g., when optic fiber 310 comprises an optic fiber in a first curved position 1110. In one or more embodiments, the first angle may comprise any angle greater than zero degrees. For example, the first angle may comprise a 45 degree angle. Illustratively, auto-fixing actuation control 720 and auto-fixing component 420 may be configured to temporarily fix auto-fixing actuation control 720 in a second fixed position within actuation control guide 810. In one or more embodiments, optic fiber 310 may comprise an optic fiber in a first curved position 1110, e.g., when auto-fixing actuation control 720 is fixed in the second fixed position within actuation control guide 810.

Figure 11C:
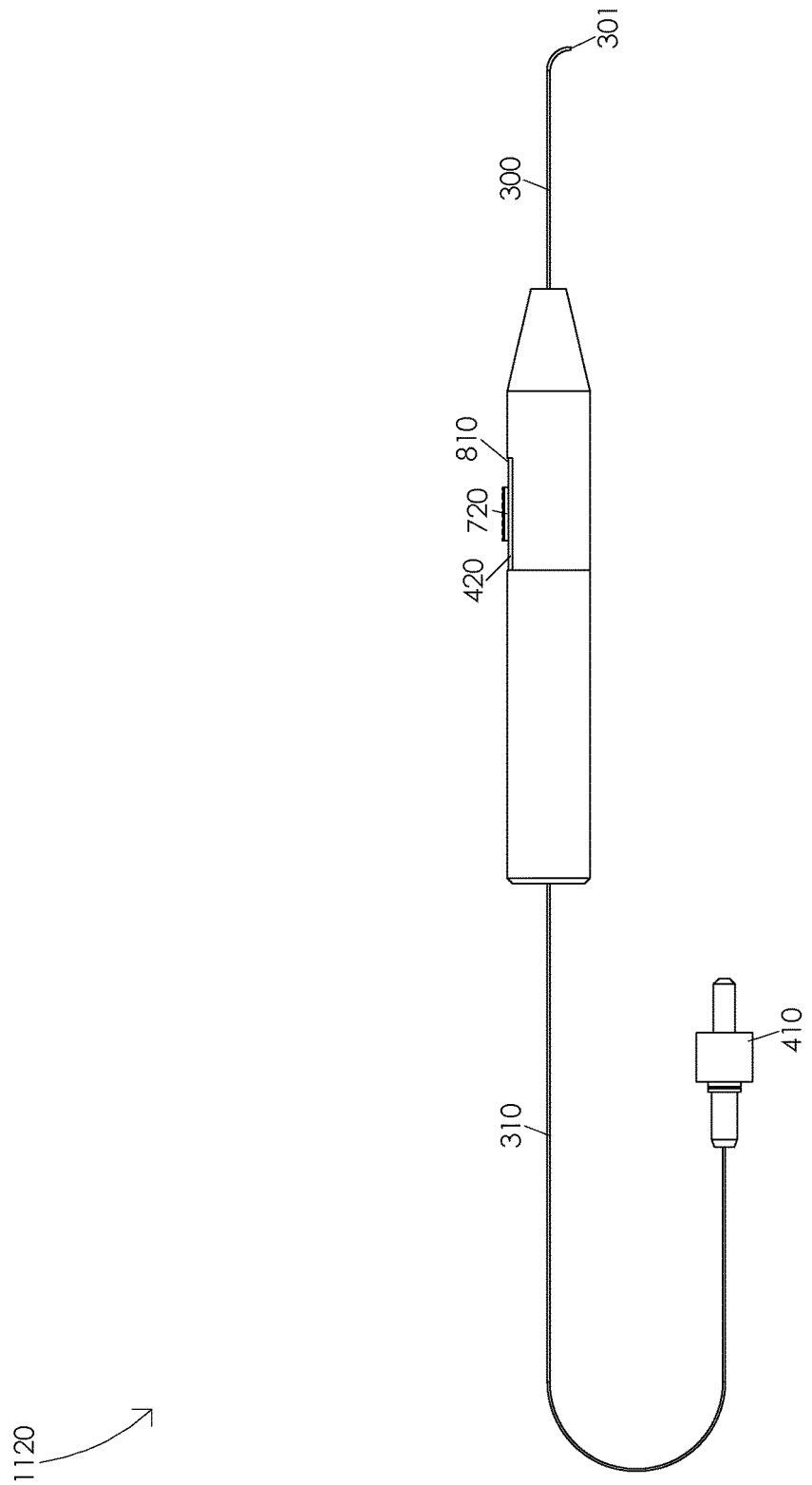

FIG. 11C illustrates an optic fiber in a second curved position 1120. In one or more embodiments, an extension of auto-fixing actuation control 720 relative to actuation control guide proximal end 812 may be configured to gradually curve optic fiber 310 from an optic fiber in a first curved position 1110 to an optic fiber in a second curved position 1120. Illustratively, an extension of auto-fixing actuation control 720 relative to actuation control guide proximal end 812 may be configured to extend actuation mechanism 710 relative to handle proximal end 802. In one or more embodiments, an extension of actuation mechanism 710 relative to handle proximal end 802 may be configured to extend flexible housing tube 300 relative to cable 910. Illustratively, a portion of cable 910, e.g., a portion of cable 910 fixed to flexible housing tube 300, may be configured to resist an extension of flexible housing tube 300 relative to cable 910. In one or more embodiments, a portion of cable 910 may be configured to apply a force to a portion of flexible housing tube 300, e.g., to resist an extension of flexible housing tube 300 relative to cable 910. Illustratively, an application of a force to a portion of flexible housing tube 300 may be configured to compress a portion of flexible housing tube 300. In one or more embodiments, a compression of a portion of flexible housing tube 300 may cause flexible housing tube 300 to gradually curve. Illustratively, a gradual curving of flexible housing tube 300 may be configured to gradually curve optic fiber 310, e.g., from an optic fiber in a first curved position 1110 to an optic fiber in a second curved position 1120. In one or more embodiments, a line tangent to optic fiber distal end 311 may intersect a line tangent to flexible housing tube proximal end 302 at a second angle, e.g., when optic fiber 310 comprises an optic fiber in a second curved position 1120. In one or more embodiments, the second angle may comprise any angle greater than the first angle. For example, the second angle may comprise a 90 degree angle. Illustratively, auto-fixing actuation control 720 and auto-fixing component 420 may be configured to temporarily fix auto-fixing actuation control 720 in a third fixed position within actuation control guide 810. In one or more embodiments, optic fiber 310 may comprise an optic fiber in a second curved position 1120, e.g., when auto-fixing actuation control 720 is fixed in the third fixed position within actuation control guide 810.

Figure 11D:
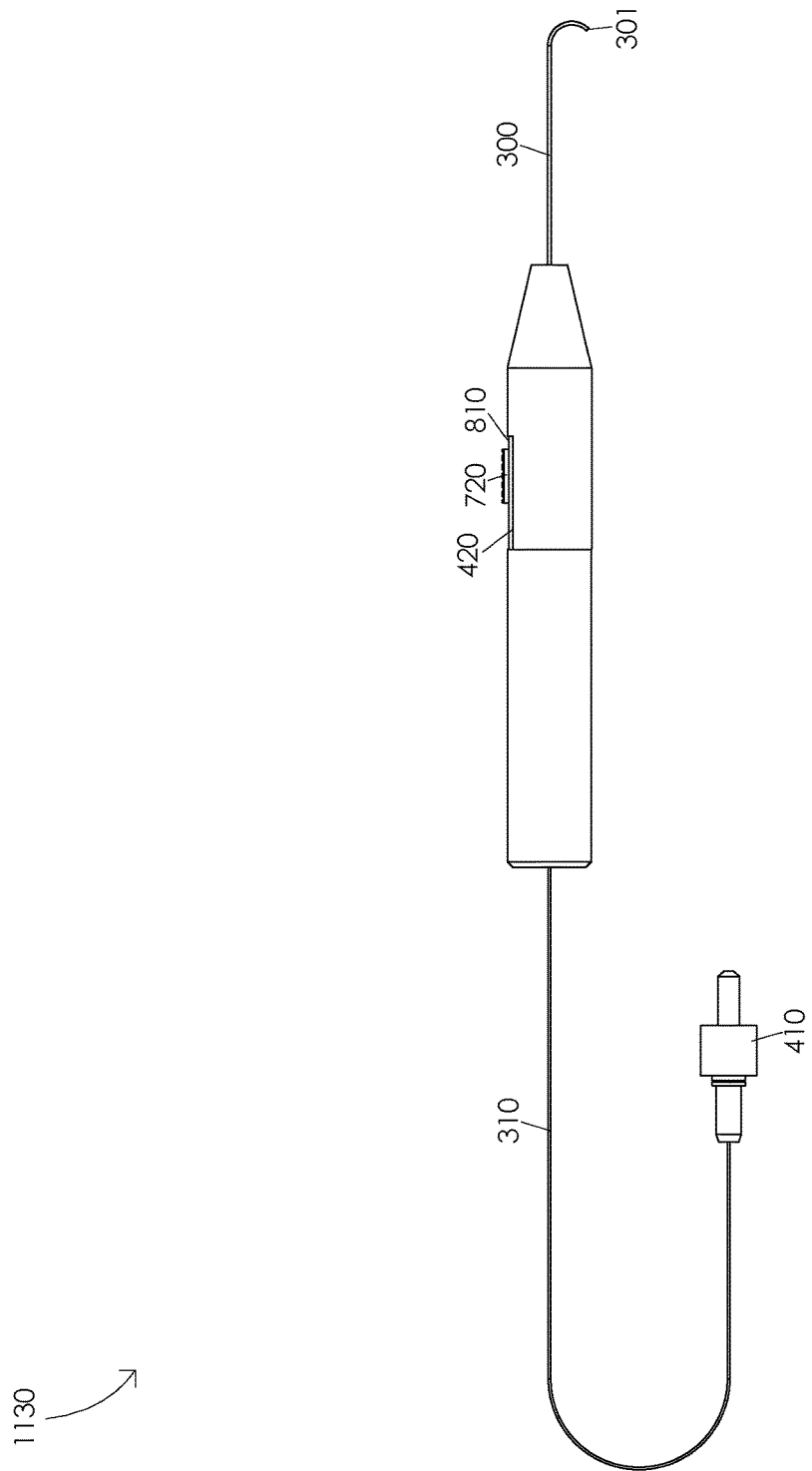

FIG. 11D illustrates an optic fiber in a third curved position 1130. In one or more embodiments, an extension of auto-fixing actuation control 720 relative to actuation control guide proximal end 812 may be configured to gradually curve optic fiber 310 from an optic fiber in a second curved position 1120 to an optic fiber in a third curved position 1130. Illustratively, an extension of auto-fixing actuation control 720 relative to actuation control guide proximal end 812 may be configured to extend actuation mechanism 710 relative to handle proximal end 802. In one or more embodiments, an extension of actuation mechanism 710 relative to handle proximal end 802 may be configured to extend flexible housing tube 300 relative to cable 910. Illustratively, a portion of cable 910, e.g., a portion of cable 910 fixed to flexible housing tube 300, may be configured to resist an extension of flexible housing tube 300 relative to cable 910. In one or more embodiments, a portion of cable 910 may be configured to apply a force to a portion of flexible housing tube 300, e.g., to resist an extension of flexible housing tube 300 relative to cable 910. Illustratively, an application of a force to a portion of flexible housing tube 300 may be configured to compress a portion of flexible housing tube 300. In one or more embodiments, a compression of a portion of flexible housing tube 300 may cause flexible housing tube 300 to gradually curve. Illustratively, a gradual curving of flexible housing tube 300 may be configured to gradually curve optic fiber 310, e.g., from an optic fiber in a second curved position 1120 to an optic fiber in a third curved position 1130. In one or more embodiments, a line tangent to optic fiber distal end 311 may intersect a line tangent to flexible housing tube proximal end 302 at a third angle, e.g., when optic fiber 310 comprises an optic fiber in a third curved position 1130. In one or more embodiments, the third angle may comprise any angle greater than the second angle. For example, the third angle may comprise a 135 degree angle. Illustratively, auto-fixing actuation control 720 and auto-fixing component 420 may be configured to temporarily fix auto-fixing actuation control 720 in a fourth fixed position within actuation control guide 810. In one or more embodiments, optic fiber 310 may comprise an optic fiber in a third curved position 1130, e.g., when auto-fixing actuation control 720 is fixed in the fourth fixed position within actuation control guide 810.

FIG. 11E illustrates an optic fiber in a fourth curved position 1140. In one or more embodiments, an extension of auto-fixing actuation control 720 relative to actuation control guide proximal end 812 may be configured to gradually curve optic fiber 310 from an optic fiber in a third curved position 1130 to an optic fiber in a fourth curved position 1140. Illustratively, an extension of auto-fixing actuation control 720 relative to actuation control guide proximal end 812 may be configured to extend actuation mechanism 710 relative to handle proximal end 802. In one or more embodiments, an extension of actuation mechanism 710 relative to handle proximal end 802 may be configured to extend flexible housing tube 300 relative to cable 910. Illustratively, a portion of cable 910, e.g., a portion of cable 910 fixed to flexible housing tube 300, may be configured to resist an extension of flexible housing tube 300 relative to cable 910. In one or more embodiments, a portion of cable 910 may be configured to apply a force to a portion of flexible housing tube 300, e.g., to resist an extension of flexible housing tube 300 relative to cable 910. Illustratively, an application of a force to a portion of flexible housing tube 300 may be configured to compress a portion of flexible housing tube 300. In one or more embodiments, a compression of a portion of flexible housing tube 300 may cause flexible housing tube 300 to gradually curve. Illustratively, a gradual curving of flexible housing tube 300 may be configured to gradually curve optic fiber 310, e.g., from an optic fiber in a third curved position 1130 to an optic fiber in a fourth curved position 1140. In one or more embodiments, a line tangent to optic fiber distal end 311 may be parallel to a line tangent to flexible housing tube proximal end 302, e.g., when optic fiber 310 comprises an optic fiber in a fourth curved position 1140. Illustratively, auto-fixing actuation control 720 and auto-fixing component 420 may be configured to temporarily fix auto-fixing actuation control 720 in a fifth fixed position within actuation control guide 810. In one or more embodiments, optic fiber 310 may comprise an optic fiber in a fourth curved position 1140, e.g., when auto-fixing actuation control 720 is fixed in the fifth fixed position within actuation control guide 810.

In one or more embodiments, one or more properties of a steerable laser probe may be adjusted to attain one or more desired steerable laser probe features. Illustratively, a distance that flexible housing tube distal end 301 extends from actuation mechanism distal end 711 may be adjusted to vary an amount of actuation of auto-fixing actuation control 720 configured to curve flexible housing tube 300 to a particular curved position. In one or more embodiments, a stiffness of flexible housing tube 300 may be adjusted to vary an amount of actuation of auto-fixing actuation control 720 configured to curve flexible housing tube 300 to a particular curved position. Illustratively, a stiffness of flexible housing tube 300 may be adjusted to vary a bend radius of flexible housing tube 300. In one or more embodiments, a stiffness of flexible housing tube 300 may be adjusted to vary a radius of curvature of flexible housing tube 300, e.g., when flexible housing tube 300 is in a particular curved position.

In one or more embodiments, at least a portion of optic fiber 310 may be enclosed in an optic fiber sleeve configured to, e.g., protect optic fiber 310, vary a stiffness of optic fiber 310, vary an optical property of optic fiber 310, etc. Illustratively, optic fiber 310 may comprise a buffer, a cladding disposed in the buffer, and a core disposed in the cladding. In one or more embodiments, at least a portion of optic fiber 310 may comprise a buffer configured to protect an optical property of optic fiber 310. Illustratively, at least a portion of optic fiber 310 may comprise a buffer configured to protect an optical layer of optic fiber 310, e.g., the buffer may protect an optical layer of a curved portion of optic fiber 310. In one or more embodiments, at least a portion of optic fiber 310 may comprise a polyimide buffer configured to protect an optical property of optic fiber 310. For example, at least a portion of optic fiber 310 may comprise a Kapton buffer configured to protect an optical property of optic fiber 310.

In one or more embodiments, a location wherein cable 910 may be fixed to flexible housing tube 300 may be adjusted to vary an amount of actuation of auto-fixing actuation control 720 configured to curve flexible housing tube 300 to a particular curved position. For example, a portion of cable 910 may be fixed to an outer portion of flexible housing tube 300. Illustratively, cable 910 may be fixed to flexible housing tube 300 at a plurality of fixation points, e.g., to vary one or more properties of a steerable laser probe. In one or more embodiments, a length of cable 910 may be adjusted to vary an amount of actuation of auto-fixing actuation control 720 configured to curve flexible housing tube 300 to a particular curved position. Illustratively, a steerable laser probe may comprise one or more redundant cables 910. In one or more embodiments, one or more redundant cables 910 may be configured to maintain a particular curved position of flexible housing tube 300, e.g., in the event that cable 910 breaks or fails. Illustratively, one or more redundant cables 910 may be configured to maintain a particular curved position of flexible housing tube 300, e.g., in the event that a cable 910 fixation means fails. In one or more embodiments, one or more redundant cables 910 may be configured to maintain a particular curved position of flexible housing tube 300, e.g., in the event that cable 910 is no longer configured to maintain the particular curved position of flexible housing tube 300. Illustratively, one or more redundant cables 910 may be configured to maintain a particular curved position of flexible housing tube 300 wherein cable 910 is also configured to maintain the particular curved position of flexible housing tube 300.

In one or more embodiments, flexible housing tube 300 may comprise an access window configured to allow access to a portion cable 910. Illustratively, cable 910 may be fixed to a portion of flexible housing tube 300, e.g., by looping a portion of cable 910 through an aperture in flexible housing tube 300. In one or more embodiments, cable 910 may be fixed to a portion of flexible housing tube 300, e.g., by a purely mechanical means. For example, cable 910 may be fixed to a portion of flexible housing tube 300 in a manner other than by an adhesive, a weld, etc. Illustratively, cable 910 may be fixed to a portion of flexible housing tube 300 wherein a portion of cable 910 is configured to fail at a first applied failure force and a fixation means that fixes a portion of cable 910 to a portion of flexible housing tube 300 is configured to fail at a second applied failure force. In one or more embodiments, the second applied failure force may be greater than the first applied failure force.

Illustratively, a steerable laser probe may be configured to indicate, e.g., to a surgeon, a direction that optic fiber 310 may curve, e.g., due to an actuation of auto-fixing actuation control 720 within actuation control guide 810. In one or more embodiments, a portion of a steerable laser probe, e.g., handle 800, may be marked in a manner configured to indicate a direction that optic fiber 310 may curve. For example, a portion of flexible housing tube 300 may comprise a mark configured to indicate a direction that optic fiber 310 may curve. Illustratively, flexible housing tube 300 may comprise a slight curve, e.g., a curve less than 7.5 degrees, when auto-fixing actuation control 720 is fully retracted relative to actuation control guide proximal end 812. For example, flexible housing tube 300 may comprise a slight curve, e.g., a curve greater than 7.5 degrees, when auto-fixing actuation control 720 is fully retracted relative to actuation control guide proximal end 812. In one or more embodiments, flexible housing tube 300 may comprise a slight curve configured to indicate a direction that optic fiber 310 may curve, e.g., due to an actuation of auto-fixing actuation control 720 within actuation control guide 810.

Figure 12A:
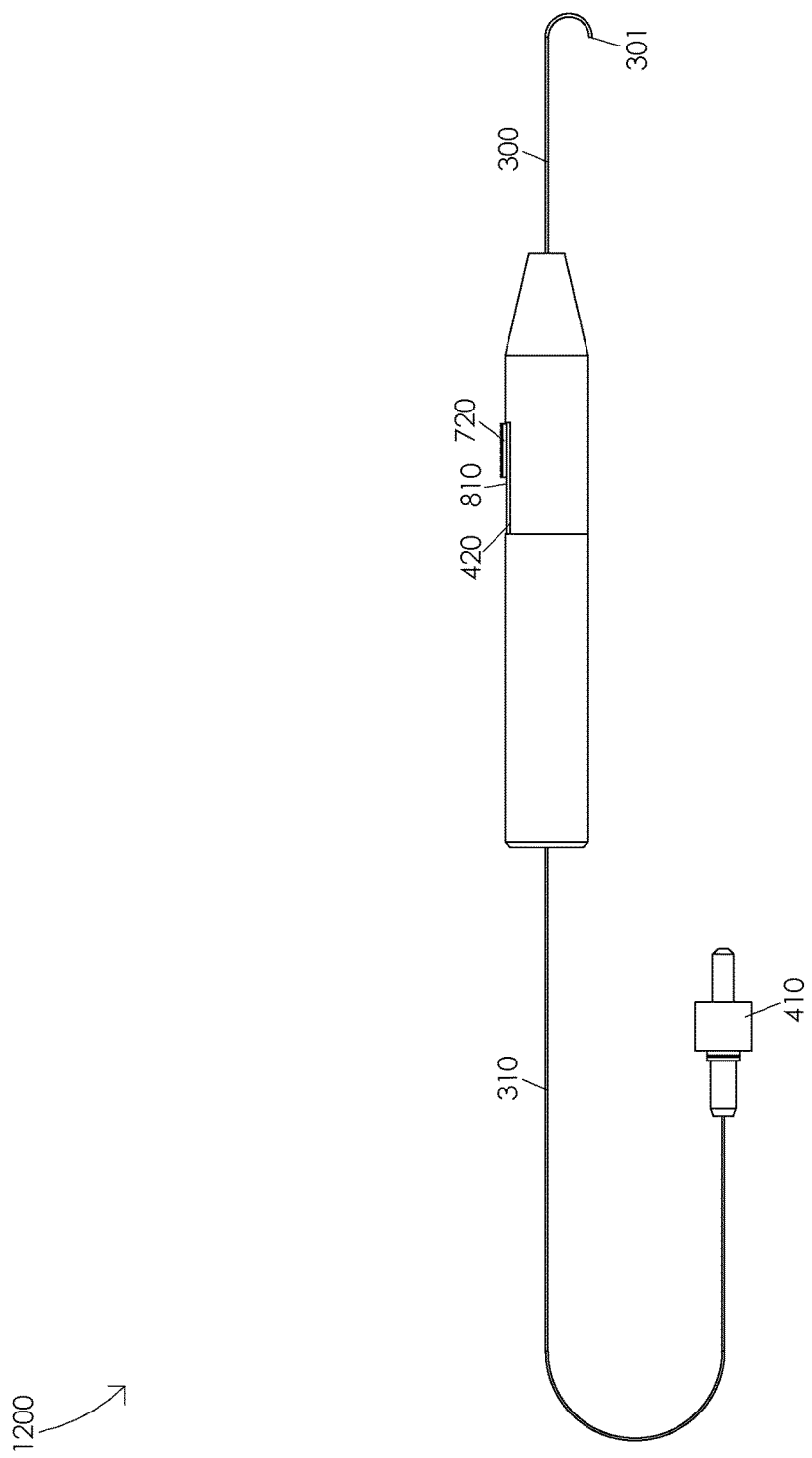
FIGS. 12A, 12B, 12C, 12D, and 12E are schematic diagrams illustrating a gradual straightening of an optic fiber.

FIGS. 12A, 12B, 12C, 12D, and 12E are schematic diagrams illustrating a gradual straightening of an optic fiber 310. FIG. 12A illustrates a fully curved optic fiber 1200. In one or more embodiments, optic fiber 310 may comprise a fully curved optic fiber 1200, e.g., when auto-fixing actuation control 720 is fully extended relative to actuation control guide proximal end 812. Illustratively, optic fiber 310 may comprise a fully curved optic fiber 1200, e.g., when actuation mechanism 710 is fully extended relative to handle proximal end 802. In one or more embodiments, a line tangent to optic fiber distal end 311 may be parallel to a line tangent to flexible housing tube proximal end 302, e.g., when optic fiber 310 comprises a fully curved optic fiber 1200.

Figure 12B:
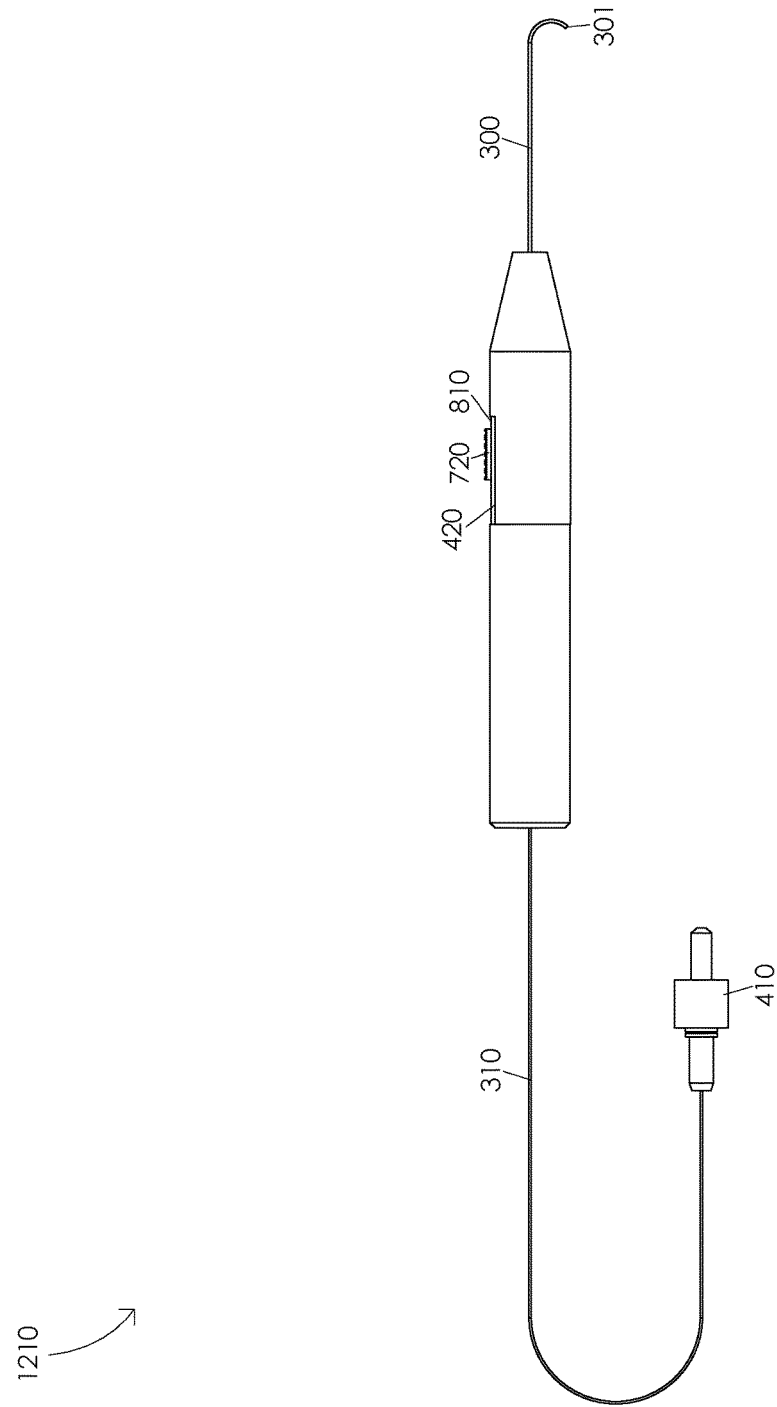

FIG. 12B illustrates an optic fiber in a first partially straightened position 1210. In one or more embodiments, a retraction of auto-fixing actuation control 720 relative to actuation control guide proximal end 812 may be configured to gradually straighten optic fiber 310 from a fully curved optic fiber 1200 to an optic fiber in a first partially straightened position 1210. Illustratively, a retraction of auto-fixing actuation control 720 relative to actuation control guide proximal end 812 may be configured to retract actuation mechanism 710 relative to handle proximal end 802. In one or more embodiments, a retraction of actuation mechanism 710 relative to handle proximal end 802 may be configured to retract flexible housing tube 300 relative to cable 910. Illustratively, a portion of cable 910, e.g., a portion of cable 910 fixed to flexible housing tube 300, may be configured to facilitate a retraction of flexible housing tube 300 relative to cable 910. In one or more embodiments, a portion of cable 910 may be configured to reduce a force applied to a portion of flexible housing tube 300, e.g., due to a retraction of flexible housing tube 300 relative to cable 910. Illustratively, a reduction of a force applied to a portion of flexible housing tube 300 may be configured to decompress a portion of flexible housing tube 300. In one or more embodiments, a decompression of a portion of flexible housing tube 300 may cause flexible housing tube 300 to gradually straighten. Illustratively, a gradual straightening of flexible housing tube 300 may be configured to gradually straighten optic fiber 310, e.g., from a fully curved optic fiber 1200 to an optic fiber in a first partially straightened position 1210. In one or more embodiments, a line tangent to optic fiber distal end 311 may intersect a line tangent to flexible housing tube proximal end 302 at a first partially straightened angle, e.g., when optic fiber 310 comprises an optic fiber in a first partially straightened position 1210. Illustratively, the first partially straightened angle may comprise any angle less than 180 degrees. For example, the first partially straightened angle may comprise a 135 degree angle.

Figure 12C:
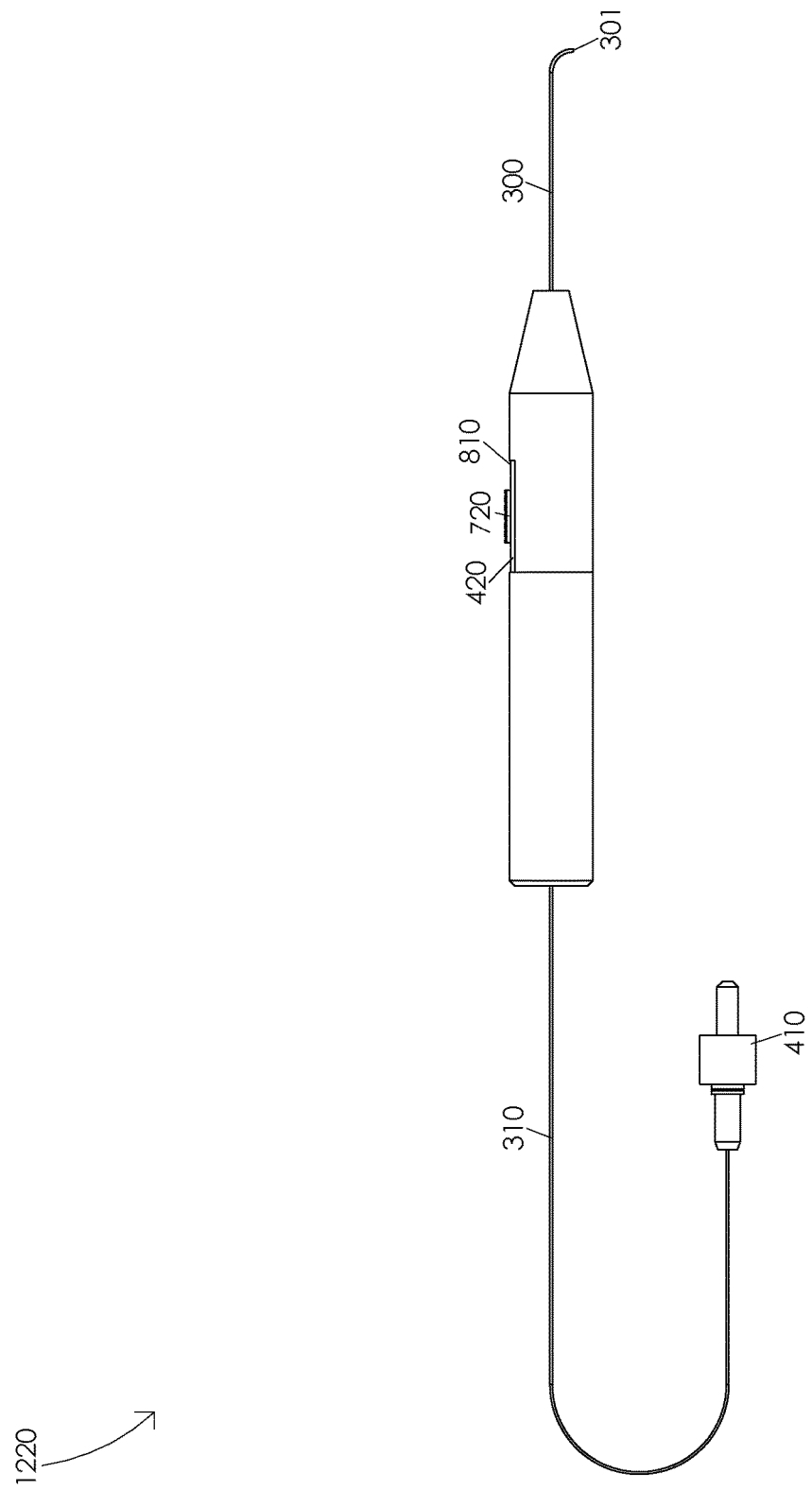

FIG. 12C illustrates an optic fiber in a second partially straightened position 1220. In one or more embodiments, a retraction of auto-fixing actuation control 720 relative to actuation control guide proximal end 812 may be configured to gradually straighten optic fiber 310 from an optic fiber in a first partially straightened position 1210 to an optic fiber in a second partially straightened position 1220. Illustratively, a retraction of auto-fixing actuation control 720 relative to actuation control guide proximal end 812 may be configured to retract actuation mechanism 710 relative to handle proximal end 802. In one or more embodiments, a retraction of actuation mechanism 710 relative to handle proximal end 802 may be configured to retract flexible housing tube 300 relative to cable 910. Illustratively, a portion of cable 910, e.g., a portion of cable 910 fixed to flexible housing tube 300, may be configured to facilitate a retraction of flexible housing tube 300 relative to cable 910. In one or more embodiments, a portion of cable 910 may be configured to reduce a force applied to a portion of flexible housing tube 300, e.g., due to a retraction of flexible housing tube 300 relative to cable 910. Illustratively, a reduction of a force applied to a portion of flexible housing tube 300 may be configured to decompress a portion of flexible housing tube 300. In one or more embodiments, a decompression of a portion of flexible housing tube 300 may cause flexible housing tube 300 to gradually straighten. Illustratively, a gradual straightening of flexible housing tube 300 may be configured to gradually straighten optic fiber 310, e.g., from an optic fiber in a first partially straightened position 1210 to an optic fiber in a second partially straightened position 1220. In one or more embodiments, a line tangent to optic fiber distal end 311 may intersect a line tangent to flexible housing tube proximal end 302 at a second partially straightened angle, e.g., when optic fiber 310 comprises an optic fiber in a second partially straightened position 1220. Illustratively, the second partially straightened angle may comprise any angle less than the first partially straightened angle. For example, the second partially straightened angle may comprise a 90 degree angle.

Figure 12D:
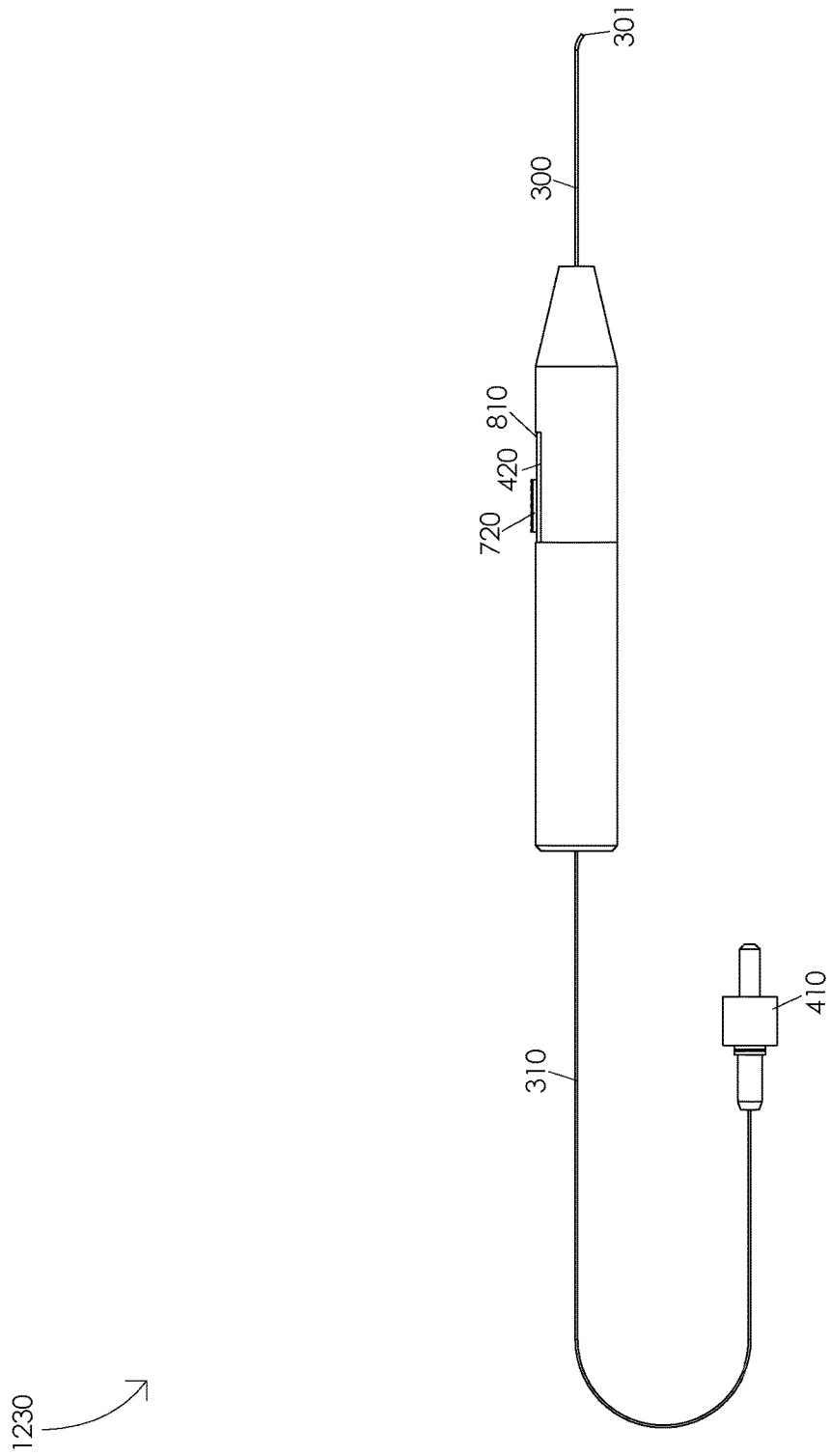

FIG. 12D illustrates an optic fiber in a third partially straightened position 1230. In one or more embodiments, a retraction of auto-fixing actuation control 720 relative to actuation control guide proximal end 812 may be configured to gradually straighten optic fiber 310 from an optic fiber in a second partially straightened position 1220 to an optic fiber in a third partially straightened position 1230. Illustratively, a retraction of auto-fixing actuation control 720 relative to actuation control guide proximal end 812 may be configured to retract actuation mechanism 710 relative to handle proximal end 802. In one or more embodiments, a retraction of actuation mechanism 710 relative to handle proximal end 802 may be configured to retract flexible housing tube 300 relative to cable 910. Illustratively, a portion of cable 910, e.g., a portion of cable 910 fixed to flexible housing tube 300, may be configured to facilitate a retraction of flexible housing tube 300 relative to cable 910. In one or more embodiments, a portion of cable 910 may be configured to reduce a force applied to a portion of flexible housing tube 300, e.g., due to a retraction of flexible housing tube 300 relative to cable 910. Illustratively, a reduction of a force applied to a portion of flexible housing tube 300 may be configured to decompress a portion of flexible housing tube 300. In one or more embodiments, a decompression of a portion of flexible housing tube 300 may cause flexible housing tube 300 to gradually straighten. Illustratively, a gradual straightening of flexible housing tube 300 may be configured to gradually straighten optic fiber 310, e.g., from an optic fiber in a second partially straightened position 1220 to an optic fiber in a third partially straightened position 1230. In one or more embodiments, a line tangent to optic fiber distal end 311 may intersect a line tangent to flexible housing tube proximal end 302 at a third partially straightened angle, e.g., when optic fiber 310 comprises an optic fiber in a third partially straightened position 1230. Illustratively, the third partially straightened angle may comprise any angle less than the second partially straightened angle. For example, the third partially straightened angle may comprise a 45 degree angle.

Figure 12E:
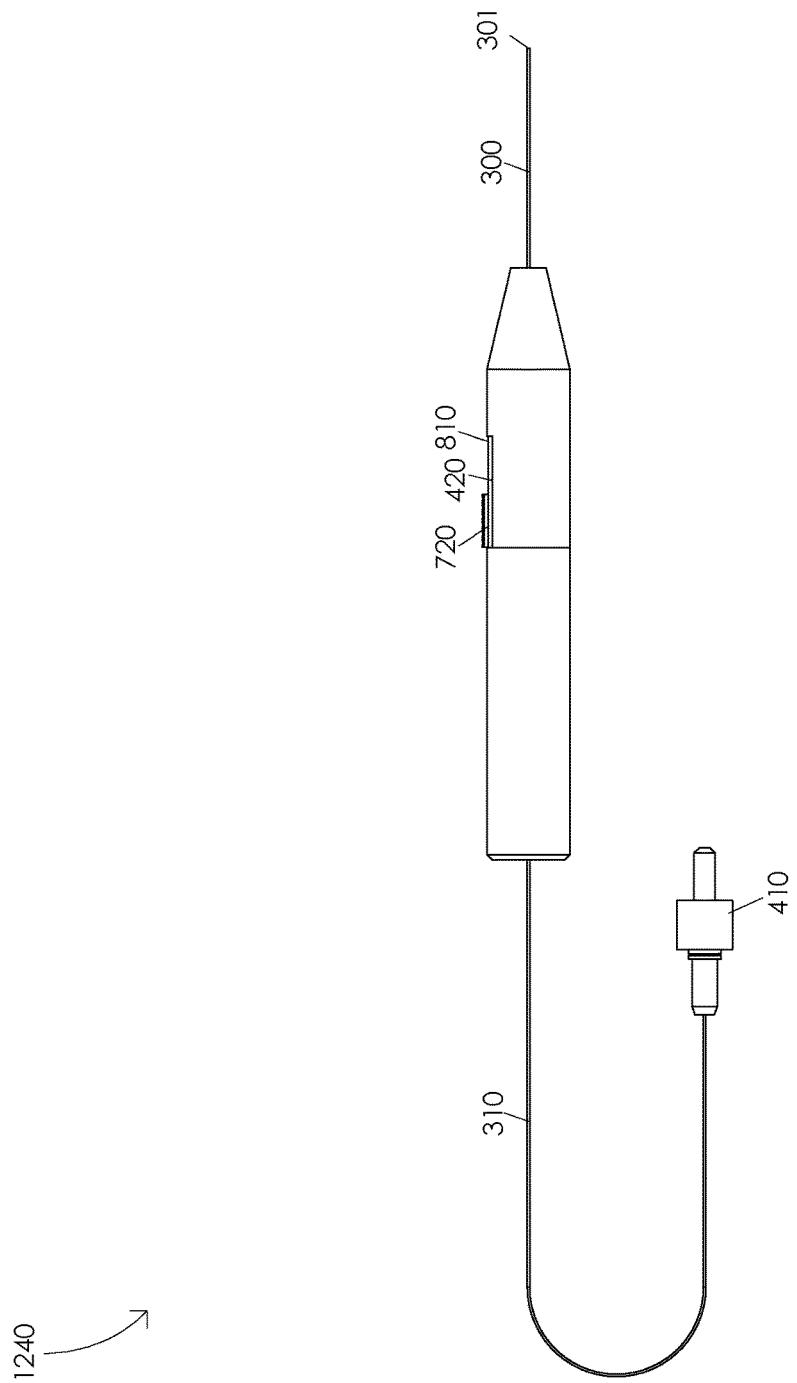

FIG. 12E illustrates an optic fiber in a fully straightened position 1240. In one or more embodiments, a retraction of auto-fixing actuation control 720 relative to actuation control guide proximal end 812 may be configured to gradually straighten optic fiber 310 from an optic fiber in a third partially straightened position 1230 to an optic fiber in a fully straightened position 1240. Illustratively, a retraction of auto-fixing actuation control 720 relative to actuation control guide proximal end 812 may be configured to retract actuation mechanism 710 relative to handle proximal end 802. In one or more embodiments, a retraction of actuation mechanism 710 relative to handle proximal end 802 may be configured to retract flexible housing tube 300 relative to cable 910. Illustratively, a portion of cable 910, e.g., a portion of cable 910 fixed to flexible housing tube 300, may be configured to facilitate a retraction of flexible housing tube 300 relative to cable 910. In one or more embodiments, a portion of cable 910 may be configured to reduce a force applied to a portion of flexible housing tube 300, e.g., due to a retraction of flexible housing tube 300 relative to cable 910. Illustratively, a reduction of a force applied to a portion of flexible housing tube 300 may be configured to decompress a portion of flexible housing tube 300. In one or more embodiments, a decompression of a portion of flexible housing tube 300 may cause flexible housing tube 300 to gradually straighten. Illustratively, a gradual straightening of flexible housing tube 300 may be configured to gradually straighten optic fiber 310, e.g., from an optic fiber in a third partially straightened position 1230 to an optic fiber in a fully straightened position 1240. In one or more embodiments, a line tangent to optic fiber distal end 311 may be parallel to a line tangent to flexible housing tube proximal end 302, e.g., when optic fiber 310 comprises an optic fiber in a fully straightened position 1240.

Illustratively, a surgeon may aim optic fiber distal end 311 at any of a plurality of targets within an eye, e.g., to perform a photocoagulation procedure, to illuminate a surgical target site, etc. In one or more embodiments, a surgeon may aim optic fiber distal end 311 at any target within a particular transverse plane of the inner eye by, e.g., rotating handle 800 to orient flexible housing tube 300 in an orientation configured to cause a curvature of flexible housing tube 300 within the particular transverse plane of the inner eye and varying an amount of actuation of auto-fixing actuation control 720 within actuation control guide 810. Illustratively, a surgeon may aim optic fiber distal end 311 at any target within a particular sagittal plane of the inner eye by, e.g., rotating handle 800 to orient flexible housing tube 300 in an orientation configured to cause a curvature of flexible housing tube 300 within the particular sagittal plane of the inner eye and varying an amount of actuation of auto-fixing actuation control 720 within actuation control guide 810. In one or more embodiments, a surgeon may aim optic fiber distal end 311 at any target within a particular frontal plane of the inner eye by, e.g., varying an amount of actuation of auto-fixing actuation control 720 within actuation control guide 810 to orient a line tangent to optic fiber distal end 311 wherein the line tangent to optic fiber distal end 311 is within the particular frontal plane of the inner eye and rotating handle 800. Illustratively, a surgeon may aim optic fiber distal end 311 at any target located outside of the particular transverse plane, the particular sagittal plane, and the particular frontal plane of the inner eye, e.g., by varying a rotational orientation of handle 800 and varying an amount of actuation of auto-fixing actuation control 720 within actuation control guide 810. In one or more embodiments, a surgeon may aim optic fiber distal end 311 at any target of a plurality of targets within an eye, e.g., without increasing a length of a portion of a steerable laser probe within the eye. Illustratively, a surgeon may aim optic fiber distal end 311 at any target of a plurality of targets within an eye, e.g., without decreasing a length of a portion of a steerable laser probe within the eye.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of a surgical instrument, the teachings of the present invention are equally suitable to any systems where the functionality may be employed. Therefore, it is the object of the appended claims to cover all such variations and modifications as come within the true spirit and scope of the invention.

What is claimed is:

1. A laser probe comprising:
   an optic fiber having an optic fiber distal end and an optic fiber proximal end;
   a single flexible housing tube having a flexible housing tube distal end and a flexible housing tube proximal end;
   a handle having a handle distal end and a handle proximal end wherein the flexible housing tube distal end extends from the handle distal end;
   a handle base of the handle having a handle base distal end and a handle base proximal end;
   a handle end cap of the handle having a handle end cap distal end and a handle end cap proximal end;
   a flexible housing tube guide of the handle;
   an actuation control guide of the handle having an actuation control guide distal end and an actuation control guide proximal end;
   an actuation mechanism guide of the handle;
   an actuation mechanism having an actuation mechanism distal end and an actuation mechanism proximal end wherein the actuation mechanism is disposed in the actuation mechanism guide between the handle end cap proximal end and the handle base distal end;
   an inner bore of the actuation mechanism;
   a flexible housing tube housing of the actuation mechanism wherein the flexible housing tube is disposed in the flexible housing tube guide and the flexible housing tube housing and wherein the flexible housing tube is fixed in the flexible housing tube housing;
   an auto-fixing actuation control of the actuation mechanism wherein the auto-fixing actuation control is disposed in the actuation control guide and wherein an actuation of the auto-fixing actuation control towards the actuation control guide distal end and away from the actuation control guide proximal end is configured to extend the actuation mechanism relative to the handle proximal end wherein the actuation mechanism actuates towards the handle distal end and away from the handle proximal end and wherein the actuation of the auto-fixing actuation control towards the actuation control guide distal end and away from the actuation control guide proximal end is configured to extend the flexible housing tube housing relative to the handle proximal end and extend the flexible housing tube relative to the optic fiber proximal end; and
   an auto-fixing component wherein the auto-fixing component is disposed in an auto-fixing component housing of the handle and wherein a portion of the auto-fixing component is adjacent to a portion of the auto-fixing actuation control.

2. The laser probe of claim 1 wherein the actuation of the auto-fixing actuation control towards the actuation control guide distal end and away from the actuation control guide proximal end is configured to curve the optic fiber to a first curved position.

3. The laser probe of claim 2 wherein the auto-fixing component is configured to temporarily fix the optic fiber in the first curved position.

4. The laser probe of claim 3 wherein the actuation of the auto-fixing actuation control towards the actuation control guide distal end and away from the actuation control guide proximal end is configured to curve the optic fiber to a second curved position.

5. The laser probe of claim 2 wherein the auto-fixing component is configured to temporarily fix the optic fiber in the second curved position.

6. The laser probe of claim 1 wherein the actuation of the auto-fixing actuation control towards the actuation control guide distal end and away from the actuation control guide proximal end is configured to curve the flexible housing tube to a first curved position.

7. The laser probe of claim 6 wherein the auto-fixing component is configured to temporarily fix the flexible housing tube in the first curved position.

8. The laser probe of claim 7 wherein the actuation of the auto-fixing actuation control towards the actuation control guide distal end and away from the actuation control guide proximal end is configured to curve the flexible housing tube to a second curved position.

9. The laser probe of claim 8 wherein the auto-fixing component is configured to temporarily fix the flexible housing tube in the second curved position.

10. The laser probe of claim 1 further comprising:
    a cable having a cable distal end and a cable proximal end wherein the cable is disposed in the flexible housing tube and the handle.

11. The laser probe of claim 10 wherein the cable is configured to resist the flexible housing tube from extending relative to the optic fiber.

12. The laser probe of claim 1 further comprising:
    a distal chamber of the handle.

13. The laser probe of claim 1 further comprising:
    an optic fiber housing of the handle.

14. The laser probe of claim 1 wherein an actuation of the auto-fixing actuation control towards the actuation control guide proximal end and away from the actuation control guide distal end is configured to straighten the optic fiber to a first straightened position.

15. The laser probe of claim 14 wherein the auto-fixing component is configured to temporarily fix the optic fiber in the first straightened position.

16. The laser probe of claim 15 wherein the actuation of the auto-fixing actuation control towards the actuation control guide proximal end and away from the actuation control guide distal end is configured to straighten the optic fiber to a second straightened position.

17. The laser probe of claim 16 wherein the auto-fixing component is configured to temporarily fix the optic fiber in the second straightened position.

18. The laser probe of claim 1 wherein an actuation of the auto-fixing actuation control towards the actuation control guide proximal end and away from the actuation control guide distal end is configured to straighten the flexible housing tube to a first straightened position.

19. The laser probe of claim 18 wherein the auto-fixing component is configured to temporarily fix the flexible housing tube in the first straightened position.

20. The laser probe of claim 19 wherein the actuation of the auto-fixing actuation control towards the actuation control guide proximal end and away from the actuation control guide distal end is configured to straighten the flexible housing tube to a second straightened position and wherein the auto-fixing component is configured to temporarily fix the flexible housing tube in the second straightened position.

* * * * *